United States Patent
Brieaddy et al.

[11] Patent Number: 5,998,400
[45] Date of Patent: Dec. 7, 1999

[54] HYPOLIPIDEMIC BENZOTHIAZEPINES

[75] Inventors: Lawrence Edward Brieaddy, Raleigh; Anthony Louis Handlon; Gordon Lewis Hodgson, Jr., both of Durham, all of N.C.

[73] Assignee: Glaxo Wellcome Inc., Research Triangle Park, N.C.

[21] Appl. No.: 08/836,405

[22] PCT Filed: Nov. 16, 1995

[86] PCT No.: PCT/GB95/02700

§ 371 Date: May 1, 1997

§ 102(e) Date: May 1, 1997

[87] PCT Pub. No.: WO96/16051

PCT Pub. Date: May 30, 1996

[30] Foreign Application Priority Data

Nov. 17, 1994 [GB] United Kingdom .................. 9423172

[51] Int. Cl.⁶ ........................ C07D 281/10; A61K 31/55
[52] U.S. Cl. ........................ 514/211; 540/491; 540/552
[58] Field of Search .................. 540/491, 552; 514/211

[56] References Cited

U.S. PATENT DOCUMENTS 5,610,153   3/1997   Buhlmayer et al. ............. 514/211
5,817,653   10/1998  Elliot et al. .................. 514/213

FOREIGN PATENT DOCUMENTS

| | | |
|---|---|---|
| 0 612 737 A1 | 8/1994 | European Pat. Off. . |
| 0 617 971 A1 | 9/1994 | European Pat. Off. . |
| 0 395 302 A1 | 10/1994 | European Pat. Off. . |
| 2141027 | 12/1984 | United Kingdom . |
| 2 255 937 | 11/1992 | United Kingdom . |
| 92/21668 | 12/1992 | WIPO . |
| 93/16055 | 8/1993 | WIPO . |
| WO 9316055 | 8/1993 | WIPO . |
| 94/13651 | 6/1994 | WIPO . |
| 94/18183 | 8/1994 | WIPO . |
| 94/18184 | 8/1994 | WIPO . |
| WO95/04534 | 2/1995 | WIPO . |
| 96/05188 | 2/1996 | WIPO . |
| 98/38182 | 9/1998 | WIPO . |

OTHER PUBLICATIONS

Ried et al., Liebigs Ann. Chem. (1980), (8), 1252–1258.
Ried et al., Liebigs Ann. Chem. (1980), (11), 1913–1916.

*Primary Examiner*—Richard L. Raymond
*Assistant Examiner*—Bruck Kifle
*Attorney, Agent, or Firm*—Lorie Ann Morgan

[57] ABSTRACT

The invention is concerned with novel hypolipidemic compounds of formula (I), with processes and novel intermediates for their preparation, pharmaceutical compositions containing them and with their use in medicine, particularly in the prophylaxis and treatment of hyperlipidemic conditions, and associated diseases such as atherosclerosis.

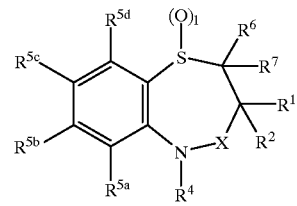

(I)

15 Claims, No Drawings

HYPOLIPIDEMIC BENZOTHIAZEPINES

This application is filed pursuant to 35 U.S.C. §371 as a United States National Phase Application of International Application No. PCT/GB95/02700 filed Nov. 16, 1995 which claims priority from GB9423172.7 filed Nov. 17, 1994.

The present invention is concerned with new hypolipidemic compounds, with processes and novel intermediates for their preparation, with pharmaceutical compositions containing them and with their use in medicine, particularly in the prophylaxis and treatment of hyperlipidemic conditions and associated conditions such as atherosclerosis.

Hyperlipidemic conditions are often associated with elevated plasma concentrations of low density lipoprotein (LDL) cholesterol. Such concentrations can be reduced by decreasing the absorption of bile acids from the intestine. One method by which this may be achieved is to inhibit the bile acid active uptake system in the terminal ileum. Such inhibition stimulates the conversion of cholesterol to bile acid by the liver and the resulting increase in demand for cholesterol produces a corresponding increase in the rate of clearance of LDL cholesterol from the blood plasma or serum.

A novel class of heterocyclic compounds has been identified which reduce the plasma or serum concentrations of LDL cholesterol and in consequence are particularly useful as hypolipidemic agents. By decreasing the concentrations of cholesterol and cholesterol ester in the plasma, the compounds of the present invention retard the build-up of atherosclerotic lesions and reduce the incidence of coronary heart disease-related events. The latter are defined as cardiac events associated with increased concentrations of cholesterol and cholesterol ester in the plasma or serum.

International Patent Application No. WO 93/16055 describes 1,4-benzothiazepine compounds which have hypolipidemic activity. A group of novel substituted 1,5-benzothiazepine compounds has now been discovered which also have hypolipidemic activity.

Accordingly, the present invention provides compounds of the formula (I)

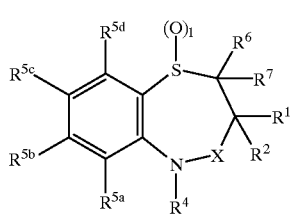

(I)

wherein $R^1$ and $R^2$ are the same or different and each is optionally substituted $C_{1-6}$ alkyl, $C_{3-6}$ cycloalkyl, or $R^1$ and $R^2$ together with the carbon atom to which they are attached form an optionally substituted $C_{3-6}$ spiro-cycloalkyl group;

$R^4$ is a $C_{6-14}$ aryl, or a $C_{3-13}$ heteroaryl group each optionally substituted with one to eight substituents which are the same or different and are each selected from halogen, hydroxy, nitro, phenyl-$C_{1-6}$ alkoxy, $C_{1-6}$ alkoxy, optionally substituted $C_{1-6}$ alkyl, $S(O)_nR^8$, $SO_2NR^8R^9$, $CO_2R^8$, $O(CH_2CH_2O)_nR^8$, $OSO_7R^8$, $O(CH_2)_pSO_3R^8$, $O(CH_2)_pNR^9R^{10}$ and $O(CH_2)_pN^+R^9R^{10}R^{11}$ wherein $R^8$ to $R^{11}$ are the same or different and are independently selected from hydrogen or optionally substituted $C_{1-6}$ alkyl, and wherein p is an integer from 1–4 and n is an integer from 0–3;

$R^{5a}$, $R^{5b}$, $R^{5c}$, and $R^{5d}$ each represent atoms or groups which are the same or different and each is hydrogen, halogen, cyano, $R^8$-acetylide, $OR^8$, optionally substituted $C_{1-6}$ alkyl, $COR^8$, $CH(OH)R^8$, $S(O)_nR^8$, $SO_2NR^8R^9$, $P(O)(OR^8)_2$, $OCOR^8$, $OCF_3$, $OCN$, $SCN$, $NHCN$, $CH_2OR^8$, $CHO$, $(CH_2)_pCN$, $CONR^9R^{10}$, $(CH_2)_pCOR^8$, $(CH_2)_pNR^9R^{10}$, $CO_2R^8$, $NHCOCF_3$, $NHSO_2R^8$, $OCH_2OR^8$, $OCH=CHR^8$, $O(CH_2CH_2O)_nR^8$, $OSO_2R^8$, $O(CH_2)_pSO_3R^8$, $O(CH_2)_pNR^9R^{10}$ and $O(CH_2)_pN^+R^9R^{10}R^{11}$ wherein $R^8$ to $R^{11}$, n, and p are as hereinbefore defined; or $R^{5a}$ and $R^{5b}$, $R^{5b}$ and $R^{5c}$, or $R^{5c}$ and $R^{5d}$ together with the ring to which they are attached form a cyclic group —$O(CR^9R^{10})_mO$— wherein $R^9$ and $R^{10}$ are as hereinbefore defined and m is 1 or 2;

$R^6$ and $R^7$ are the same or different and each is hydrogen, optionally substituted $C_{1-6}$ alkyl, $C_{3-6}$ cycloalkyl, or $R^6$ and $R^7$ together with the carbon atom to which they are attached form an optionally substituted $C_{3-6}$ spiro-cycloalkyl group;

X is $CH_2$, C=O, C=S, or C=$NR^8$ wherein $R^8$ is as hereinbefore defined; and l is an integer from 0–2; and salts, solvates or a physiologically functional derivatives thereof.

Suitably $R^1$ is a $C_{1-6}$ alkyl group. Preferably $R^1$ is methyl, ethyl or n-propyl and most preferably $R^1$ is ethyl.

Suitably $R^2$ is a $C_{1-6}$ alkyl group. Preferably $R^2$ is methyl, ethyl, n-propyl, n-butyl or n-pentyl and most preferably $R^2$ is ethyl or n-butyl.

Suitably $R^4$ is a phenyl group optionally substituted with one to five, preferably one or two, substituents which are the same or different and are each selected from halogen, hydroxy, nitro, phenyl-$C_{1-6}$ alkoxy, $C_{1-6}$ alkoxy, optionally substituted $C_{1-6}$ alkyl, $S(O)_nR^8$, $CO_2R^8$, $O(CH_2CH_2O)_nR^8$, $OSO_2R^8$, $O(CH_2)_pSO_3R^8$, $O(CH_2)_pNR^9R^{10}$ and $O(CH_2)_pN^+R^9R^{10}R^{11}$, preferably halogen, hydroxy, nitro, phenyl-$C_{1-6}$ alkoxy, $C_{1-6}$alkoxy, or optionally substituted $C_{1-6}$ alkyl. Preferably $R^4$ is phenyl optionally substituted at the 3- and/or 4-position by halogen, hydroxy, methyl, ethyl, methoxy, ethoxy, trifluoromethyl, hydroxy, carboxy or $O(CH_2)_3SO_3H$. Most preferably $R^4$ is unsubstituted phenyl or phenyl substituted at the 3- and/or 4-positions with halogen, hydroxy or $C_{1-6}$ alkoxy, for example, methoxy or ethoxy.

Suitably $R^{5a}$, $R^{5b}$, $R^{5c}$, and $R^{5d}$ are the same or different and are each hydrogen, $C_{1-4}$ alkoxy, halogen, hydroxy or $C_{1-4}$ alkyl optionally substituted by fluoro. Preferably $R^{5a}$, $R^{5b}$, $R^{5c}$, and $R^{5d}$ are the same or different and are each hydrogen, methyl, methoxy, hydroxy, trifluoromethyl or halo. More preferably $R^{5a}$ and $R^{5d}$ are hydrogen and $R^{5b}$ and $R^{5c}$ are the same or different and are each hydrogen, $C_{1-4}$ alkoxy, halogen hydroxy, or $C_{1-4}$ alkyl optionally substituted by fluoro. Most preferably $R^{5a}$ and $R^{5d}$ are hydrogen and $R^{5b}$ and $R^{5c}$ are the same or different and are each hydrogen, methyl, methoxy, hydroxy, trifluoromethyl or halo.

Suitably $R^6$ and $R^7$ are the same or different and are each hydrogen or a $C_{1-6}$ alkyl group, for example, methyl or ethyl. Most preferably, $R^6$ and $R^7$ are both hydrogen.

Suitably X is $CH_2$ or C=O.

Suitably $R^9$ to $R^{11}$ are the same or different and are each hydrogen or methyl.

Suitably l is 0 or 2, and is preferably 2.

When one or more of $R^1$, $R^2$, $R^4$ to $R^{11}$ is a substituted $C_{1-6}$ alkyl group, or comprises a $C_{1-6}$ alkyl group the substituents may be the same or different and each is selected from hydroxy, halogen, $C_{1-6}$ alkyl, $C_{1-6}$ alkoxy, $COR^{12}$, nitrile, $CO_2R^{12}$, $SO_3R^{12}$, $NR^{13}R^{14}$, $N^+R^{13}R^{14}R^{15}$ wherein $R^{12}$ to $R^{15}$ are the same or different and each is selected from hydrogen or $C_{1-6}$ alkyl preferably methyl.

Further preferred compounds of formula (I) are:
(±)-3-n-Butyl-3-ethyl-2,3-dihydro-5-phenyl-1,5-benzothiazepin-4-one;
(±)-3-n-Butyl-3-ethyl-2,3-dihydro-5-phenyl-1,5-benzothiazepin-4-one-1,1-dioxide;
(±)-3-n-Butyl-3-ethyl-2,3,4,5-tetrahydro-5-phenyl-1,5-benzothiazepine;
(±)-3-n-Butyl-3-ethyl-2,3,4,5-tetrahydro-5-phenyl-1,5-benzothiazepine-1,1-dioxide;
(±)-3-n-Butyl-2-isobutyl-3-ethyl-2,3,4,5-tetrahydro-5-phenyl-1,5-benzothiazepine-1,1-dioxide;
3,3-Diethyl-2,3-dihydro-5-phenyl-1,5-benzothiazepin-4-one;
3,3-Diethyl-2,3-dihydro-5-phenyl-1,5-benzothiazepin-4-one 1,1-dioxide;
3,3-Diethyl-2,3,4,5-tetrahydro-5-phenyl-1,5-benzothiazepine;
3,3-Diethyl-2,3,4,5-tetrahydro-5-phenyl-1,5-benzothiazepine-1,1-dioxide;
3,3-Dimethyl-2,3-dihydro-5-phenyl-1,5-benzothiazepin-4-one;
3,3-Dimethyl-2,3-dihydro-5-phenyl-1,5-benzothiazepin-4-one-1,1-dioxide;
3,3-Dimethyl-2,3,4,5-tetrahydro-5-phenyl-1,5-benzothiazepine;
3,3-Dimethyl-2,3,4,5-tetrahydro-5-phenyl-1,5-benzothiazepine-1,1-dioxide
(±)-3-n-Butyl-3-ethyl-2,3,4,5-tetrahydro-7,8-dimethoxy-5-phenyl-1,5-benzothiazepine-1,1-dioxide;
3,3-Diethyl-2,3,4,5-tetrahydro-7,8-dimethoxy-5-phenyl-1,5-benzothiazepine-1,1-dioxide;
(±)-3-n-Butyl-3-ethyl-2,3,4,5-tetrahydro-8-methoxy-5-phenyl-1,5-benzothiazepine-1,1-dioxide;
3,3-Diethyl-2,3,4,5-tetrahydro-8-methoxy-5-phenyl-1,5-benzothiazepine-1,1-dioxide;
(±)-3-n-Butyl-3-ethyl-2,3,4,5-tetrahydro-5-phenyl-1,5-benzothiazepin-8-ol-1,1-dioxide;
3,3-Diethyl-2,3,4,5-tetrahydro-5-phenyl-1,5-benzothiazepin-8-ol-1,1-dioxide;
(±)-3-n-Butyl-3-ethyl-2,3,4,5-tetrahydro-7-methoxy-5-phenyl-1,5-benzothiazepin-8-ol-1,1-dioxide;
3,3-Diethyl-2,3,4,5-tetrahydro-7-methoxy-5-phenyl-1,5-benzothiazepin-8-ol-1,1-dioxide;
(±)-7-bromo-3-n-Butyl-3-ethyl-2,3,4,5-tetrahydro-8-methoxy-5-phenyl-1,5-benzothiazepine-1,1-dioxide;
7-bromo-3,3-Diethyl-2,3,4,5-tetrahydro-8-methoxy-5-phenyl-1,5-benzothiazepine-1,1-dioxide;
(±)-3-n-Butyl-3-ethyl-2,3,4,5-tetrahydro-5-phenyl-1,5-benzothiazepin-7,8-diol-1,1-dioxide;
3,3-Diethyl-2,3,4,5-tetrahydro-5-phenyl-1,5-benzothiazepin-7,8-diol-1,1-dioxide;
(±)-3-n-Butyl-3-ethyl-2,3,4,5-tetrahydro-8-methoxy-5-phenyl-1,5-benzothiazepine-1-monoxide;
3,3-Diethyl-2,3,4,5-tetrahydro-8-methoxy-5-phenyl-1,5-benzothiazepine-1-monoxide;
(±)-3-n-Butyl-3-ethyl-2,3,4,5-tetrahydro-5-phenyl-1,5-benzothiazepin-8-ol-1-monoxide;
3,3-Diethyl-2,3,4,5-tetrahydro-5-phenyl-1,5-benzothiazepin-8-ol-1-monoxide;
(±)-3-n-Butyl-3-ethyl-2,3-dihydro-8-methoxy-5-phenyl-1,5-benzothiazepin-4-one;
(±)-3-n-Butyl-3-ethyl-2,3,4,5-tetrahydro-8-methoxy-5-phenyl-1,5-benzothiazepine;
(±)-3-n-Butyl-3-ethyl-2,3,4,5-tetrahydro-8-methoxy-5-phenyl-1,5-benzothiazepine-1,1-dioxide;
(±)-3-n-Butyl-3-ethyl-2,3,4,5-tetrahydro-8-hydroxy-5-phenyl-1,5-benzothiazepine-1,1-dioxide;
(±)-7-Bromo-3-n-butyl-3-ethyl-2,3-dihydro-8-methoxy-5-phenyl-1,5-benzothiazepin-4-one;
(±)-7-Bromo-3-n-butyl-3-ethyl-2,3,4,5-tetrahydro-8-methoxy-5-phenyl-1,5-benzothiazepine 1,1-dioxide;
(±)-7-Bromo-3-n-butyl-3-ethyl-2,3,4,5-tetrahydro-5-phenyl-1,5-benzothiazepin-8-ol 1,1-dioxide;
(±)-3-n-butyl-3-ethyl-2,3,4,5-tetrahydro-7-methoxy-5-phenyl-1,5-benzothiazepin-8-ol 1,1-dioxide;
(±)-3-n-butyl-3-ethyl-2,3,4,5-tetrahydro-7,8-dimethoxy-5-phenyl-1,5-benzothiazepine 1,1-dioxide;
(±)-3-n-butyl-3-ethyl-2,3,4,5-tetrahydro-5-phenyl-1,5-benzothiazepine-7,8-diol 1,1-dioxide;
(±)-7-Bromo-3-n-butyl-3-ethyl-2,3-dihydro-5-phenyl-1,5-benzothiazepin-4-one;
(±)-3-n-butyl-3-ethyl-2,3,4,5-tetrahydro-7-methoxy-5-phenyl-1,5-benzothiazepine 1,1-dioxide; and
(±)-3-n-butyl-3-ethyl-2,3,4,5-tetrahydro-5-phenyl-1,5-benzothiazepin-7-ol 1,1-dioxide.

Particularly preferred compounds include:
(±)-3-n-butyl-3-ethyl-2,3,4,5-tetrahydro-7-methoxy-5-phenyl-1,5-benzothiazepin-8-ol 1,1-dioxide; and
(±)-3-n-Butyl-3-ethyl-2,3,4,5-tetrahydro-8-hydroxy-5-phenyl-1,5-benzothiazepine-1,1-dioxide.

Pharmaceutically acceptable salts are particularly suitable for medical applications because of their greater aqueous solubility relative to the parent, i.e., basic, compounds. Such salts must clearly have a pharmaceutically acceptable anion or cation. Suitable pharmaceutically acceptable acid addition salts of the compounds of the present invention include those derived from inorganic acids, such as hydrochloric, hydrobromic, phosphoric, metaphosphoric, nitric, sulphonic and sulphuric acids, and organic acids, such as acetic, benzenesulphonic, benzoic, citric, ethanesulphonic, fumaric, gluconic, glycolic, isothionic, lactic, lactobionic, maleic, malic, methanesulphonic, succinic, p-toluenesulphonic, tartaric and trifluoroacetic acids. The chloride salt is particularly preferred for medical purposes. Suitable pharmaceutically acceptable base salts include ammonium salts, alkali metal salts, such as sodium and potassium salts, and alkaline earth salts, such as magnesium and calcium salts.

Salts having a non-pharmaceutically acceptable anion are within the scope of the invention as useful intermediates for the preparation or purification of pharmaceutically acceptable salts and/or for use in non-therapeutic, for example, in vitro, applications.

Any references to "compound(s) of formula (I)", "compounds of the present invention", "compounds according to the invention" etc., refer to compound(s) of formula (I) as described above together with their salts, solvates and physiologically functional derivatives as defined herein.

The term "physiologically functional derivative" as used herein refers to any physiologically acceptable derivative of a compound of the present invention, for example, an ester, which upon administration to a mammal, such as a human, is capable of providing (directly or indirectly) such a compound or an active metabolite thereof A further aspect of the present invention is prodrugs of the compounds of the invention. Such prodrugs can be metabolised in vivo to give a compound according to the invention. These prodrugs may or may not be active in their own right.

The compounds of the present invention can also exist in different polymorphic forms, for example, amorphous and crystalline polymorphic forms. All polymorphic forms of the compounds of the present invention are within the scope of the invention and are a further aspect thereof.

The term "alkyl" as used herein refers, unless otherwise stated, to a monovalent straight or branched chain radical. Likewise, the terms "cycloalkyl" and "spiro-cycloalkyl" refer, unless otherwise stated, to a divalent cyclic or spiro-cyclic radical respectively. The term "alkoxy" refers to a monovalent straight or branched chain radical attached to the parent molecular moiety through an oxygen atom. The term "aryl" refers to a monovalent mono-, bi- or tri-cyclic aromatic ring. The term "heteroaryl" refers to a monovalent mono-, bi- or tri-cyclic aromatic ring comprising one or more heteroatoms(e.g., nitrogen, oxygen, sulfur). The term "phenylalkoxy" refers to a monovalent phenyl group attached to a divalent $C_{1-6}$ alkylene group which is itself attached to the parent molecular moiety through an oxygen atom. The term "halo" refers to fluoro, chloro, bromo, or iodo.

The compounds of formula (I) exist in forms wherein the carbon centres —$C(R^1)(R^2)$— and —$C(R^6)(R^7)$— can be chiral. The present invention includes within its scope each possible optical isomer substantially free, i.e. as associated with less than 5%, of any other optical isomer(s), and mixtures of one or more optical isomers in any proportions, including racemic mixtures.

In those cases where the absolute stereochemistry at —$C(R^1)(R^2)$— and —$C(R^6)(R^7)$— has not been determined, the compounds of the invention are defined in terms of the relative positions of the $R^1/R^2$ and $R^6R^7$ substituents. Thus, those compounds wherein the bulkier of the substituents, i.e the substituent of higher mass are both located on the same side of the thiazepine ring are referred to herein as "cis", and those compounds in which the bulkier of the substituents are located on opposite sides of the ring are referred to as "trans." It will be evident to a skilled person that both "cis" and "trans" compounds of the invention can each exist in two enantiomeric forms which are individually designated "(+)-" or "(−)-" according to the direction of rotation of a plane of polarised light when passed through a sample of the compound. Cis or trans compounds of the invention in which the individual enantiomers have not been resolved are referred to herein using the prefix "(+−)-".

According to further aspects of the invention, there are also provided:
(a) the compounds of formula (I) and pharmaceutically acceptable salts, solvates and physiologically functional derivatives thereof for use as therapeutic agents, particularly in the prophylaxis and treatment of clinical conditions for which a bile acid uptake inhibitor is indicated, for example, a hyperlipidemic condition, and associated diseases such as atherosclerosis;
(b) pharmaceutical compositions comprising a compound of formula (I) or one of its pharmaceutically acceptable salts, solvates, or physiologically functional derivatives, at least one pharmaceutically acceptable carrier and, optionally, one or more other physiologically active agents;
(c) the use of a compound of formula (I) or of a pharmaceutically acceptable salt, solvate, or physiologically functional derivative thereof in the manufacture of a medicament for the prophylaxis or treatment of a clinical condition for which a bile acid uptake inhibitor is indicated, for example, a hyperlipidemic condition, and associated diseases such as atherosclerosis;
(d) a method of inhibiting the absorption of bile acids from the intestine of a mammal, such as a human, which comprises administering an effective bile acid absorption inhibiting amount of a compound of formula (I) or of a pharmaceutically acceptable salt, solvate, or physiologically functional derivative thereof to the mammal;
(e) a method of reducing the blood plasma or serum concentrations of LDL cholesterol in a mammal, such as a human, which comprises administering an effective cholesterol reducing amount of a compound of formula (I) or of a pharmaceutically acceptable salt, solvate, or physiologically functional derivative thereof to the mammal;
(f) a method of reducing the concentrations of cholesterol and cholesterol ester in the blood plasma or serum of a mammal, such as a human, which comprises administering an effective cholesterol and cholesterol ester reducing amount of a compound of formula (I) or of a pharmaceutically acceptable salt, solvate, or physiologically functional derivative thereof to the mammal;
(g) a method of increasing the fecal excretion of bile acids in a mammal, such as a human, which comprises administering an effective bile acid fecal excretion increasing amount of a compound of formula (I) or of a pharmaceutically acceptable salt, solvate, or physiologically functional derivative thereof to the mammal;
(h) a method for the prophylaxis or treatment of a clinical condition in a mammal, such as a human, for which a bile acid uptake inhibitor is indicated, for example, a hyperlipidemic condition, and associated diseases such as atherosclerosis, which comprises administering a therapeutically effective amount of a compound of the formula (I) or of a pharmaceutically acceptable salt, solvate, or physiologically functional derivative thereof to the mammal;
(i) a method of reducing the incidence of coronary heart disease-related events in a mammal, such as a human, which comprises administering an effective coronary heart disease-related events reducing amount of a compound of formula (I) or of a pharmaceutically acceptable salt, solvate, or physiologically functional derivative thereof;
(j) a method of reducing the concentration of cholesterol in the blood plasma or serum of a mammal, such as a human, which comprises administering an effective cholesterol reducing amount of a compound of formula (I);
(k) processes for the preparation of compounds of formula (I) (including salts, solvates and physiologically functional derivatives thereof as defined herein);
(l) novel chemical intermediates in the preparation of compounds of formula (I); and
(m) the compounds of synthetic Examples 1–27 as hereinafter disclosed.

The amount of a compound of formula (I) which is required to achieve the desired biological effect will, of course, depend on a number of factors, for example, the specific compound chosen, the use for which it is intended, the mode of administration and the clinical condition of the recipient. In general, a daily dose is in the range of from 0.001 mg to 100 mg (typically from 0.01 mg to 50 mg) per day per kilogram bodyweight, for example, 0.01–10 mg/kg/day. Thus, orally administrable unit dose formulations, such as tablets or capsules, may contain, for example, from 0.1 to 100 mg, typically from 0.1 to 10 mg, preferably 0.1 to 5 mg. In the case of pharmaceutically acceptable salts, the weights indicated above refer to the weight of the benzothiazepine ion derived from the salt.

For the prophylaxis or treatment of the conditions referred to above, the compounds of formula (I) can be used as the compound per se, but are preferably presented with an acceptable carrier in the form of a pharmaceutical composition. The carrier must, of course, be acceptable in the sense of being compatible with the other ingredients of the composition and must not be deleterious to the recipient. The carrier can be a solid or a liquid, or both, and is preferably formulated with the compound as a unit-dose composition, for example, a tablet, which can contain from 0.05% to 95% by weight of the active compound. Other pharmacologically active substances can also be present including other compounds of formula (I). The pharmaceutical compositions of the invention can be prepared by any of the well known techniques of pharmacy consisting essentially of admixing the components.

Pharmaceutical compositions according to the present invention include those suitable for oral, rectal, topical, buccal (e.g. sub-lingual) and parenteral (e.g. subcutaneous, intramuscular, intradermal, or intravenous) administration, although the most suitable route in any given case will depend on the nature and severity of the condition being treated and on the nature of the particular compound of formula (I) which is being used. Enteric-coated and enteric-coated controlled release formulations are also within the scope of the invention. Suitable enteric coatings include cellulose acetate phthalate, polyvinylacetate phthalate, hydroxypropylmethylcellulose phthalate and anionic polymers of methacrylic acid and methacrylic acid methyl ester. Suitable enteric coated and enteric coated controlled release formulations include tablets and capsules.

Pharmaceutical compositions suitable for oral administration can be presented in discrete units, such as capsules, cachets, lozenges, or tablets, each containing a predetermined amount of a compound of formula (I); as a powder or granules; as a solution or a suspension in an aqueous or non-aqueous liquid; or as an oil-in-water or water-in-oil emulsion. As indicated, such compositions can be prepared by any suitable method of pharmacy which includes the step of bringing into association the active compound and the carrier (which can constitute one or more accessory ingredients). In general, the compositions are prepared by uniformly and intimately admixing the active compound with a liquid or finely divided solid carrier, or both, and then, if necessary, shaping the product. For example, a tablet can be prepared by compressing or moulding a powder or granules of the compound, optionally with one or more accessory ingredients. Compressed tablets can be prepared by compressing, in a suitable machine, the compound in a free-flowing form, such as a powder or granules optionally mixed with a binder, lubricant, inert diluent and/or surface active/dispersing agent(s). Moulded tablets can be made by moulding, in a suitable machine, the powdered compound moistened with an inert liquid diluent. Controlled release tablets can be prepared in similar manner and with the addition of, for example, hydroxypropylmethyl cellulose.

Enteric-coated tablets can be prepared by coating the tablets with an enteric polymer such as cellulose acetate phthalate, polyvinylacetate phthalate, hydroxypropylmethyl-cellulose phthalate, or anionic polymers of methacrylic acid and methacrylic acid methyl ester (Eudragit L™). Except for Eudragit L, these polymers should also include 10% (by weight of the quantity of polymer used) of a plasticizer to prevent membrane cracking during application or on storage. Suitable plasticizers include diethyl phthalate, tributyl citrate and triacetin.

Enteric-coated controlled release tablets can be prepared by coating controlled release tablets with an enteric polymer such as cellulose acetate phthalate, polyvinylacetate phthalate, hydroxypropylmethyl-cellulose phthalate, or anionic polymers of methacrylic acid and methacrylic acid methyl ester (Eudragit L). Except for Eudragit L, these polymers should also include 10% (by weight of the quantity of polymer used) of a plasticizer to prevent membrane cracking during application or on storage. Suitable plasticizers include diethyl phthalate, tributyl citrate and triacetin.

Capsules can be prepared by admixing a compound of formula (I) with, for example, magnesium stearate, pregelantinised starch, sodium starch glycollate, and/or magnesium stearate and filling two-part hard gelatin capsules with the resulting mixture.

Controlled release capsule compositions can be prepared by admixing a compound of formula (I) with, for example, microcrystalline cellulose and/or lactose, extruding using an extruder, then spheronising and drying the extrudate. The dried pellets are coated with a release controlling membrane, for example ethyl cellulose, and filled into two-part, hard gelatin capsules.

Enteric capsule compositions can be prepared by admixing a compound of formula (I) with, for example, microcrystalline cellulose and/or lactose, extruding using an extruder, then spheronising and drying the extrudate. The dried pellets are coated with an enteric membrane, for example cellulose acetate phthalate containing a plasticizer, for example diethyl phthalate and filled into two-part, hard gelatin capsules.

Pharmaceutical compositions suitable for buccal (sub-lingual) administration include lozenges comprising a compound of formula (I) in a flavored base, usually sucrose and acacia or tragacanth, and pastilles comprising the compound in an inert base such as gelatin and glycerin or sucrose and acacia.

Pharmaceutical compositions suitable for parenteral administration conveniently comprise sterile aqueous preparations of a compound of formula (I), preferably isotonic with the blood of the intended recipient. These preparations are preferably administered intravenously, although administration can also be effected by means of subcutaneous, intramuscular, or intradermal injection. Such preparations can conveniently be prepared by admixing the compound with water and rendering the resulting solution sterile and isotonic with the blood. Injectable compositions according to the invention will generally contain from 0.1 to 5% w/w of the active compound.

Pharmaceutical compositions suitable for rectal administration are preferably presented as unit-dose suppositories. These can be prepared by admixing a compound of formula (I) with one or more conventional solid carriers, for example, cocoa butter, and then shaping the resulting mixture.

Transdermal administration is also possible. Pharmaceutical compositions suitable for transdermal administration can be presented as discrete patches adapted to remain in intimate contact with the epidermis of the recipient for a prolonged period of time. Such patches suitably contain the active compound in an optionally buffered, aqueous solution, dissolved and/or dispersed in an adhesive, or dispersed in a polymer. A suitable concentration of the active compound is about 1% to 35%, preferably about 3% to 15%. As one particular possibility, the active compound can be delivered from the patch by electrotransport or iontophoresis, for example, as described in *Pharmaceutical Research*, 3(6), 318 (1986).

The compounds of formulas (I) can be prepared by conventional methods known to a skilled person or in an analogous manner to processes described in the art.

For example, compounds of formula (I) wherein i is 0, $R^6$ and $R^7$ are hydrogen and X is $CH_2$ can be prepared by reducing the carbonyl group of a compound formula (II)

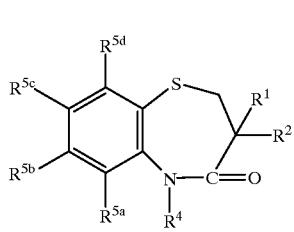

(II)

wherein $R^1, R^2, R^4$ and $R^{5a,b,c,d}$ are as hereinbefore defined using, for example, a reducing agent such as aluminum hydride ($AlH_3$), di-isobutylaluminum hydride (DEBAL) or borane ($BH_3$) in a suitable organic solvent, such as THF.

Compounds of formula II as hereinbefore defined are novel and constitute a further aspect of the present invention.

Compounds of formula (II) can be prepared by a reaction of compounds of formula III

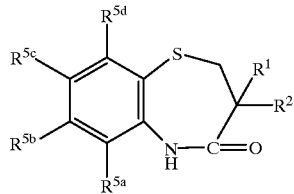

(III)

wherein $R^1, R^2$ and $R^{5a,b,c,d}$ are as hereinbefore defined, with the appropriate $R^4$-Z in the presence of a base, for example potassium carbonate ($K_2CO_3$) and optionally in the presence of a catalyst, for example, copper iodide(CiI) wherein $R^4$ is as hereinbefore defined and Z is a suitable leaving group, for example halo. The compounds $R^4$-Z are commercially available or can be prepared by methods well known or readily available to those skilled in the art.

Compounds of formula III as hereinbefore defined are novel and constitute a further aspect of the present invention.

Compounds of formula (III) can be prepared by cyclising compounds of formula (IV)

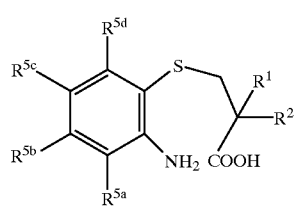

(IV)

wherein $R^1$, $R^2$ and $R^{5a,b,c,d}$ are as hereinbefore defined, by reaction with an acid, for example an organic acid such as tosic acid, preferably at an elevated temperature, for example 255° C.

Compounds of formula (IV) can be prepared by reacting compounds of formula (V) with compounds of formula (Va)

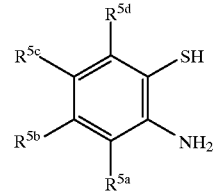

(V)

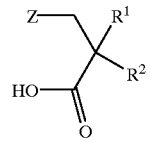

(Va)

wherein $R^1$, $R^2$ and $R^{5a,b,c,d}$ are as hereinbefore defined and Z is a suitable leaving group, for example halo, in the presence of an organic base, for example triethylamine or pyrrolidine. Compounds of formulas(V) and (Va) are commercially available or can be prepared by methods well known or readily available those skilled in the art.

Compounds of formula (I) wherein 1 is 1 or 2, can be prepared from the corresponding compound of formula (I) wherein 1 is 0 by oxidation of the thio moiety with a suitable oxidizing agent, for example, hydrogen peroxide, organic peroxy acids, Oxone® (potassium peroxymonosulfate), or osmium tetroxide ($OSO_4$).

Compounds of formula (I) wherein $R^6$ and/or $R^7$ are other than hydrogen can be prepared by treating the corresponding compound of formula (I) wherein 1 is 1 or 2 and $R^6$ and $R^7$ are hydrogen with a base, for example, n-butyllithium followed by reaction with the appropriate $R^6$-Z or $R^7$-Z wherein $R^6$ and $R^7$ are as defined herein other than hydrogen and Z is a suitable leaving group as defined herein.

Alternatively, compounds of formula (III) can be prepared from compounds of formula (VI)

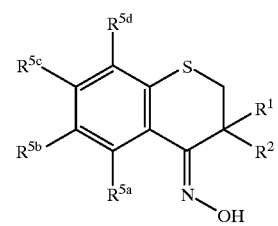

(VI)

wherein $R^1$, $R^2$ and $R^{5a,b,c,d}$ are as hereinbefore defined, by reaction with an acid, for example polyphosphoric acid at an elevated temperature, for example 120° C.

Compounds of formula (VI) can be prepared from compounds of formula (VII)

(VII)

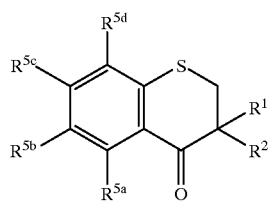

wherein $R^1$, $R^2$ and $R^{5a,b,c,d}$ are hereinbefore defined, by reaction with hydroxyl amine ($H_2NOH$).

Compounds of formula (VII) can be prepared by cyclizing compounds of formula (VIII)

(VIII)

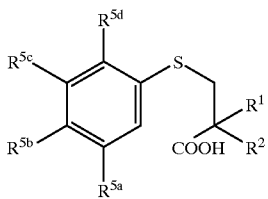

wherein $R^1$, $R^2$ and $R^{5a,b,c,d}$ are hereinbefore defined, in the presence of an acid, for example sulfuric acid ($H_2SO_4$).

Compounds of formula (VIII) can be prepared by reacting compounds of formula (IX)

(IX)

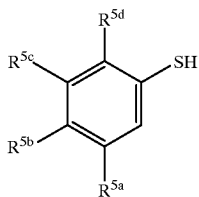

wherein $R^{5a,b,c,d}$ are as hereinbefore defined, with compounds of formula (VI) analogous to the preparation of compounds of formula (IV) described hereinbefore.

Compounds of formula (IX) are commercially available or can be prepared by methods well known or readily available to those skilled in the art.

Alternatively, compounds of formula (H) can be prepared by cyclizing compounds of formula (X)

(X)

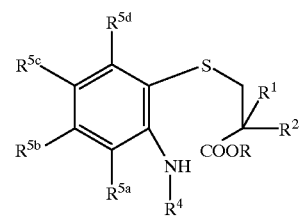

wherein $R^1$, $R^2$, $R^4$, and $R^{5a,b,c,d}$ are as hereinbefore defined, in the presence of an organic acid, for example tosic acid.

Compounds of formula (X) can be prepared from compounds of formula (XI)

(XI)

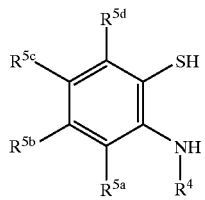

wherein $R^4$ and $R^{5a,b,c,d}$ are as herein before defined, with compounds of formula (Va) analogous to the preparation of compounds of formula (IV) described hereinbefore.

Compounds of formula (I) can be prepared by methods well known or readily available to those skilled in the art, for example by the methods disclosed in H. Gilman and J. Dietrich, J. Am. Chem. Soc., 80, 380–383 (1958).

Compounds of formula (I) wherein X is C═O can be prepared following the method for the preparation of compounds of formula (II) described hereinbefore.

Compounds of formula (I) wherein X is C═S can be prepared from the corresponding compounds of formula (I) wherein X is C═O by conversion of the C═O moiety with, for example, Lawesson's Reagent(2,4-bis(4-methoxyphenyl)-1,3-dithia-2,4-diphosphetane-2,4-disulfide).

The compounds of formula (I) substantially free, of other optical isomers can be obtained either by chiral synthesis, for example, by the use of the appropriate chiral starting material(s), such as a chiral compound of formula (Va), or by resolution of the products obtained from achiral syntheses, for example, by chiral hplc, enzymatic resolution, or by classical resolution with chiral acids.

Optional conversion of a compound of formula (I), or a compound of formula (I) comprising a basic substituent, to a corresponding acid addition salt may be effected by reaction with a solution of the appropriate acid, for example, one of those recited earlier. Optional conversion of a compound of formula (I) comprising an acidic substituent to a corresponding base salt may be effected by reaction with a solution of the appropriate base, for example, sodium hydroxide. Optional conversion to a physiologically functional derivative, such as an ester, can be carried out by methods known to those skilled in the art or obtainable from the chemical literature.

In addition, compounds of the formula (I) may be converted to different compounds of the formula (I) by standard methods known or available from the literature to those skilled in the art, for example by alkylation of a hydroxy group.

For a better understanding of the invention, the following Examples are given by way of illustration and are not to be construed in any way as limiting the scope of the invention.

General Procedures. Proton magnetic resonance spectra were recorded at 300 MHz. Mass spectra were recorded under atmospheric pressure chemical ionization (APCI) conditions on a LCMS instrument or were performed by Oneida Research Services, Inc. under chemical ionization (CI) conditions using methane as the reagent gas. Elemental Analysis were performed by Atlantic Microlab, Inc. All reactions were performed under nitrogen atmosphere. TLC plates were Whatman MK6F silica gel 60 plates and were visualized under a UV lamp. Column chromatography was performed with EM Science silica Gel 60 (230–400 mesh). Reagents were obtained from Aldrich Chemical Co. unless otherwise noted and were used without further purification. Solvents were Aldrich anhydrous grade.

EXAMPLE 1

Preparation of (±)-3-n-Butyl-3-ethyl-2,3-dihydro-5-phenyl-1,5-benzothiazepin-4-one.

(a) (1)-2-((Tert-butyldimethylsilyl)oxy)methyl-ethyl-hexanol.

To a slurry of 60% NaH (7.5 g, 187.2 mmol) in 400 ml THF was added in 3 portions 2-n-butyl-2-ethyl-1,3-propanediol (30.0 g, 187.2 mmol) and stirred for 45 min. To the resulting gum was added tert-butyldimethylsilyl chloride (28.2 g, 187.2 mmol) and stirred for 2 h. The solvent was evaporated and the residue was partitioned between water and ether. The ether layer was washed with bicarbonate solution and brine and concentrated. Column chromatography (5% ethyl acetate/petroleum ether) gave the title compound as a colorless oil (50.12 g, 182.6 mmol, 98%). $^1$H NMR (DMSO-$d_6$) δ 4.19 (t, 1H); 3.29 (s, 2H); 3.13 (d, 2H); 1.15 (m, 8H); 0.84 (s, 9H); 0.83 (t, 3H); 0.73 (t, 3H); −0.01 (s, 6H). MS Da/e=275 (MH$^+$). Calcd for $C_{15}H_{34}O_2Si$: C, 65.63; H, 12.48. Found: C, 65.87; H, 12.47.

(b) (±)-2-Ethyl-2-(hydroxymethyl)-hexanoic acid.

To a solution of the product of Example 1(a) (4.43 g, 16.0 mmol) in 16 ml $CCl_4$, 16 ml $CH_3CN$, and 24 ml $H_2O$ was added $NaIO_4$ (13.69 g, 64 mmol) and $RuCl_3$ (0.16 g, 0.8 mmol) and stirred for 16 h. The slurry was concentrated and the solvents evaporated. The residue was partitioned between $H_2O$ and $CH_2Cl_2$. The aqueous phase was extracted 3 times with $CH_2Cl_2$, dried, concentrated. The residue was dissolved in 3 ml THF, 1M tetrabutylammonium fluoride in THF (1.75 ml, 1.75 mmol) was added and the solution was stirred for 1 h. The solvent was evaporated, and the resulting oil was partitioned between $H_2O$ and $CH_2Cl_2$. The aqueous phase was extracted 3× with $CH_2Cl_2$, dried, concentrated. Column chromatography (95% $CH_2Cl_2$/4% MeOH/0.5% $H_2O$/0.5% acetic acid) gave the product as an oil 2.26 g (13.0 mmol, 81%). $^1$H NM (DMSO-$d_6$) δ 11.95 (br s, 1H); 4.74 (br s, 1H); 3.42 (s, 2H); 1.53–1.03 (m, 8H); 0.84 (t, 3H); 0.73 (t, 3H). MS Da/e=175 (MH$^+$) and 129 (M-$CO_2$H). Calcd for $C_9H_{18}O_3$: C, 62.04: H, 10.41. Found: C, 61.94; H, 10.44.

(c) (±)-2-(Bromomethyl)-2-ethyl-hexanoic acid.

A solution of the product from Example 1(b) (2.30 g, 13.2 mmol) in 48% HBr (40 ml) was refluxed for 20 h. After cooling to RT the solution was transferred to a separatory funnel, extracted 3 times with ethyl acetate, dried over $Na_2SO_4$, and concentrated. After pumping at high vacuum to remove traces of HBr, obtained the title compound (2.46 g, 10.4 mmol. 79%). $^1$H NMR (DMSO-$d_6$) δ 3.60 (s, 2H); 1.62–1.04 (m, 8H); 0.85 (t, 3H); 0.75 (t, 3H). MS Da/e=157 (M−Br), 237 (M), 238, 239 (M−2). Calcd for $C_9H_{17}O_2Br$: C, 45.59; H, 7.23; Br, 33.70. Found: C, 46.27; H, 7.17; Br, 32.94.

(d) (±)-2-(((2-Aminophenyl)thio)methyl)-2-ethylhexanoic acid.

To a solution of the product from Example 1(c) (0.52 g, 2.19 mmol) in THF (4 ml) was added 2-aminothiophenol (0.41 g, 3.29 mmol, freshly distilled) and pyrollidine (or triethylamine, 3.29 mmol) and stirred for 48 h. The reaction mixture was transferred to a separatory funnel and partitioned between $H_2O$ and $CHCl_3$. The aqueous layer was extracted 3 times with $CHCl_3$, column chromatographed (30% ethyl acetate in petroleum ether) to give the title compound (0.50 g, 1.78 mmol, 81%). $^1$H NMR (DMSO-$d_6$) δ 12.40 (br s, 1H); 7.25 (d, 1H); 7.00 (t, 1H); 6.67 (d, 1H); 6.48 (t, 1H); 5.23 (br, s, 2H); 2.91 (s, 2H); 1.66–0.99 (m, 8H); 0.77 (t, 3H); 0.67 (t, 3H). MS Da/e=282 (MH$^+$), 264 (M−$H_2O$), 236 (M−$CO_2$H). Calcd for $C_{15}H_{23}NSO_2×(0.8$ EtOAc): C, 62.12; H, 8.42; N, 3.98; S, 9.11. Found: C, 62.41; H, 8.28; N, 3.83; S, 8.91.

(e) (±)-3-n-Butyl-3-ethyl-2,3-dihydro-1,5-benzothiazepin-4-one.

A solution of the product from Example 1(d) (0.66 g, 2.35 mmol) and toluenesulfonic acid (0.15 g, 0.79 mmol) in tetradecane (30 ml) was refluxed for 3 h. After cooling to RT the reaction miture was loaded directly onto a silica column and the product eluted with 10% ethyl acetate/petroleum ether yielding the title compound (0.44 g, 167 mmol, 71%). M.P.=90.0° C. $^1$H NMR (DMSO-$d_6$) δ 9.71 (s, 1H); 7.39 (d, 1H); 7.23 (t, 1H); 7.10 (d, 1H); 6.95 (t, 1H); 2.92 (s, 2H); 1.72–1.20 (m, 4H); 1.15 (m, 4H); 0.78 (m, 6H). MS Da/e=264 (MH$^+$). Calcd for $C_{15}H_{21}NSO$: C, 68.40; H, 8.04; N, 5.32. S, 12.17. Found: C, 68.25; H, 8.11; N, 5.29; S, 12.09.

(f) (±)-3-n-Butyl-3-ethyl-2 3-dihydro-5-phenyl-1,5-benzothiazepin-4-one.

To a solution of the product from Example 1(e) (4.07 g, 15.45 mmol) in phenyl iodide (17 ml, 154 mmol) was added copper iodide (0.28 g, 1.5 mmol) and potassium carbonate (2.13 15.45 mmol), and the mixture was refluxed for 16 h. The reaction mixture was allowed to cool and was loaded directly onto a silica column and eluted with 5% ethyl acetate/petroleum ether to give the title compound (5.14 g, 15.14 mmol, 98% yield). M.P.=159.4° C. $^1$H NMR (DMSO-$d_6$) δ 7.67–6.86 (m, 9H); 3.11 (s, 2H); 1.58–1.13 (m, 8H); 0.77 (m, 6H). MS Da/e=340 (MH$^+$). Calcd for $C_{21}H_{25}NSO$: C, 74.30; H, 7.42; N, 4.13; S, 9.44. Found: C, 74.11, H, 7.49; N, 4.03; S, 9.36.

EXAMPLE 2

Preparation of (±)-3-n-Butyl-3-ethyl-2,3-dihydro-5-phenyl-1,5-benzothiazepin-4-one-1,1-dioxide.

To a solution of the compound of Example 1(f) (0.95 g, 2.80 mmol) in trifluoroacetic acid (9.5 ml) at 0° C. was added 30% hydrogen peroxide (1.60 g, 14 mmol) and stirred for 16 h. The solution was neutralized with sodium carbonate solution and the product extracted 3 times with ethyl acetate. The organic extracts were dried ($Na_2SO_4$), concentrated and the resulting oil loaded onto a silica column. The product was eluted with 20% ethyl acetate/petroleum ether giving the title compound as a white powder (0.96 g, 2.58 mmol, 92%). M.P.=57.6° C. $^1$H NMR (DMSO-$d_6$) δ 7.94–7.06 (m, 9H); 3.73 (s, 2H); 1.72–0.98 (m, 8H); 0.77 (m, 6H). MS Da/e=372 (MH$^+$). Calcd for $C_{21}H_{25}NSO_3$: C, 67.90, H, 6.78; N, 3.77; S, 8.63. Found: C, 67.61; H, 6.92; N, 3.62; S, 8.57.

EXAMPLE 3

Preparation of (±)-3-n-Butyl-3-ethyl-2,3,4,5-tetrahydro-5-phenyl-1,5-benzothiazepine.

To a solution of $AlH_3$ (44 mmol, generated in situ from $H_2SO_4$, 22 mmol, and $LiAlH_4$, 44 mmol) in 44 ml diethyl ether was added the compound of Example 1(f) (5.00 g, 14.60 mmol) in 40 ml THF at 0° C. The reaction mixture was allowed to warm to RT over 2 h and was stirred at RT for 15 h after which time TLC (20% ethyl acetate/petroleum ether) showed complete reaction. The reaction flask was cooled to 0° C. and the excess $AlH_3$ was quenched by adding 30 of $H_2O$/THF (1:2) dropwise followed by 5 ml 1M NaOH. The mixture was transferred to a separatory funnel and extracted 3 times with ether. The ether extracts were combined, dried, concentrated and column chromatographed (petroleum ether) to give the title compound (4.74 g, 14.55 mmol, 99%). $^1$H NMR (DMSO-$d_6$) δ 7.26–6.69 (m, 9H); 3.67 (br s, 2H); 2.78 (m, 2H); 1.21–1.05 (m, 8H); 0.71 (m, 6H). MS Da/e=325 (M$^+$), 326 (MH$^+$). Calcd for $C_{21}H_{27}NS$: C, 77.49; H, 8.36; N, 4.30; S, 9.85. Found: C, 77.51; H, 8.40; N, 4.31, S, 9.73.

EXAMPLE 4
Preparation of (±)-3-n-Butyl-3-ethyl-2,3,4,5-tetrahydro-5-phenyl-1,5-benzothiazepine-1,1-dioxide.

To a solution of the compound of Example 3 (4.73 g, 14.53 mmol) in 100 ml THF and 23 ml tert-butanol was added N-methyl-morpholine-N-oxide (5.1 g, 43.6 mmol) and osmium tetroxide (0.8 mmol, 2.5 wt % in 2-methyl-2-propanol). The mixture was stirred at RT for 16 h at which point 50 ml NAHCO$_3$ solution was added to neutralize any acid, the mixture transferred to a separatory funnel and extracted 3 times with ethyl acetate. The organic layers were washed with sodium hyposulfite and brine, dried (Na$_2$SO$_4$) and concentrated. Column chromatography (10% ethyl acetate/petroleum ether) yielded the title compound (4.76 g, 13.3 mmol, 92% yield). $^1$H NMR (DMSO-d$_6$) δ 7.87–6.81 (m, 9H); 3.72 (m, 2H); 3.33 (s, 2H); 1.55–0.97 (m, 8H); 0.69 (m, 6H). MS Da/e=358 (MH$^+$). Calcd for C$_{21}$H$_{27}$NSO$_2$: C, 70.55; H, 7.61; N, 3.92; S, 8.97. Found: C, 70.37; H, 7.59; N, 3.84; S, 9.07.

EXAMPLE 5
Preparation of (±)-3-n-Butyl-2-isobutyl-3-ethyl-2,3,4,5-tetrahydro-5-phenyl-1,5-benzothiazepine-1,1-dioxide.

To a solution of the compound of Example 4 (0.565 g, 1.58 mmol) in 10 ml THF was added n-butyllithium (2.5 M in THF, 1.74 mmol) at −78° C. This was stirred for 20 min at −78° C. after which iodo-2-methylpropane (1.3 M in THF, 6.32 mmol) was added dropwise at −78° C. The reaction mixture was brought up to 0° C. and stirred for 16 h. The excess base was quenched by adding brine (10 ml) and the product was extracted with ether (3×20 ml). The ether extracts were dried, concentrated and the residue applied to a silica gel column. The product was eluted with 10% ethyl acetate/petroleum ether giving a yellow oil, (0.48 g, 1.16 mmol, 74%). $^1$H NMR (DMSO-d$_6$) δ 7.89–6.80 (m, 9H); 3.30 (br m, 2H); 3.09 (br s, 1H); 1.88–0.63 (m, 23H). MS Da/e=414 (MH$^+$), 436 (M+Na). Calcd for C$_{25}$H$_{35}$NSO$_2$:1 C, 72.60; H, 8.53; N, 3.39; S, 7.75. Found: C, 72.39; H, 8.56; N, 3.27; S, 7.88.

EXAMPLE 6
Preparation of 3,3-Diethyl-2,3-dihydro-5-phenyl-1,5-benzothiazepin-4-one.

(a) 2-((Tert-butyldimethylsilyl)oxy)methyl-2-ethylbutanol.

The title compound was prepared from 2,2-diethyl-1,3-propanediol according to the procedure for Example 1(a) $^1$H NMR (DMSO-d$_6$) δ 4.20 (t, 1H); 3.29 (s, 2H); 3.14 (d, 2H); 1.13 (q, 4H); 0.84 (s, 9H); 0.73 (t, 6H); 0.73 (t, 3H); −0.01 (s, 6H). MS Da/e=247 (MH$^+$). Calcd for C$_{13}$H$_{30}$O$_2$Si: C, 63.35; H, 12.26. Found: C, 63.27; H, 12.25.

(b) 2-Ethyl-2-(hydroxymethyl)-butyric acid.

The title compound was prepared from the product of Example 6(a)(41.28 g, 189 mmol) using the procedure for Example 1(b) yielding (24.4 g, 167 mmol, 88%). $^1$H NMR (DMSO-d$_6$) δ 3.42 (s, 2H); 1.89 (s, 1H); 1.44 (q, 4H); 0.73 (t, 6H). MS Da/e=147 (MH$^+$). Calcd for C$_7$H$_{14}$O$_3$×0.3 (AcOH): C, 55.39; H, 9.33. Found: C, 55.381, R 9.17.

(c) 2-(Bromomethyl)-2-ethylbutyric acid.

The title compound was prepared from the product of Example 6(b) (22.2 g, 151 mmol) according to the procedure outlined for Example 1(c). After removing the HBr in vacuo obtained 10B (19.8 g, 94.7 mmol, 63%). $^1$H NMR (DMSO-d$_6$) δ 3.60 (s, 2H); 1.58 (q, 4H); 0.75 (t, 3H). MS Da/e=209 (M), 211 (M+2). Calcd for C$_7$H$_{13}$O$_2$Br: C, 40.21; H, 6.27; Br, 38.21. Found: C, 40.92; H, 6.38; Br, 37.17.

(d) 2-(((2-Aminophenyl)thio)methyl)-2-ethylbutyric acid.

The title compound was prepared from the compound of Example 6(c) (19.7 g, 94 mmol) according to the procedure for Example 1(d). Column chromatography yielded the product (9.77 g, 40 mmol, 43%). $^1$H NMR (DMSO-d$_6$) δ 7.24 (d, 1H); 7.00 (t, 1H); 6.69 (d, 1H); 6.49 (t, 1H); 2.91 (s, 2H); 1.60 (q, 4H); 0.68 (t, 3H). MS Da/e=254 (MH$^+$). Calcd for C$_{13}$H$_{19}$NSO$_2$: C, 61.62; H, 7.57; N, 5.52; S, 12.65. Found: C, 61.34; H, 7.62; N, 5.33; S, 12.40.

(e) 3,3-Diethyl-2,3-dihydro-1,5-benzothiazepin-4-one

The title compound was prepared by thermal ring closure of the product of Example 6(d) (9.7 g, 38 mmol) as outlined for Example 1(e). Column chromatography (50% ethyl acetate/petroleum ether) yielded the title compound (6.22 g, 26.4 mmol, 70% yield). $^1$H NMR (DMSO-d$_6$) δ 9.73 (s, 1H); 7.40 (d, 1H); 7.23 (t, 1H); 7.10 (d, 1H); 6.97 (t, 1H); 2.92 (s, 2H); 1.71–1.48 (m, 4H); 0.76 (m, 6H). MS Da/e=236 (M$^+$). Calcd for C$_{13}$H$_{17}$NSO: C, 66.34; H, 7.28; N, 5.95; S, 13.67. Found: C, 66.34; H, 7.37; N, 5.96; S, 13.58.

(f) 3,3-Diethyl-2,3-dihydro-5-phenyl-1,5-benzothiazepin-4-one.

The N-phenylation of the compound from Example 6(e) (5.40 g, 23 mmol) was accomplished following the procedure for Example 1(f) to yield the title compound after column chromatography (7.04 g, 22.6 mmol, 99% yield). M.P.=86.4° C. $^1$H NMR (DMSO-d$_6$) δ 7.66–6.87 (m, 9H); 3.09 (s, 2H); 1.45 (m, 4H); 0.76 (m, 6H). MS Da/e=312 (MH$^+$). Calcd for C$_{19}$H$_{21}$NSO: C, 73.21; H, 6.79; N, 4.49; S, 10.29. Found: C, 73.36, H, 6.90; N, 4.49; S, 10.42.

EXAMPLE 7
Preparation of 3,3-Diethyl-2,3-dihydro-5-phenyl-1,5-benzothiazepin-4-one 1,1-dioxide.

The oxidation of the compound of Example 6(f) (2.00 g, 6.4 mmol) to the sulfone was accomplished by the procedure outlined for Example 2. Column chromatography (50% ethylacetate/petroleum ether) gave the title product (1.92 g, 5.59 mmol, 88% yield). M.P.=163.0–165.6° C. $^1$H NMR (DMSO-d$_6$) δ 7.94–7.07 (m, 9H); 3.72 (s, 2H); 1.80–1.22 (br m, 4H); 0.76 (m, 6H). MS Da/e=344 (MH$^+$), 366 (M+Na$^+$). Calcd for C$_{19}$H$_{21}$NSO$_3$: C,66.44, H, 6.16 N, 4.07; S, 9.33. Found: C, 66.22; H, 6.21; N, 4.06; S, 9.42.

EXAMPLE 8
Preparation of 3,3-Diethyl-2,3,4,5-tetrahydro-5-phenyl-1,5-benzothiazepine The reduction of the compound of Example 6(f) (2.43 g, 7.80 mmol) was accomplished by the procedure outlined for Example 3. Column chromatography (20% ethylacetate/petroleum ether) gave the title product (2.01 g, 6.76 mmol, 87% yield). $^1$H NMR (DMSO-d$_6$) δ 7.29–6.71 (m, 9H); 3.65 (br s, 2H); 2.77 (s, 2H); 1.36–1.15 (m, 4H); 0.67 (m, 6H). MS Da/e=298 (MH$^+$). Calcd. for C$_{19}$H$_{23}$NS: C, 76.71; H, 7.79 N, 4.70; S, 10.77. Found: C, 76.64; H, 7.82; N, 4.69; S, 10.72.

EXAMPLE 9
Preparation of 3,3-Diethyl-2,3,4,5-tetrahydro-5-phenyl-1,5-benzothiazepine-1,1-dioxide.

The oxidation of the compound of Example 8 (0.53 g, 1.80 mmol) was accomplished by the procedure outlined for Example 4. Column chromatography (50% ethyl acetate/petroleum ether) gave the title product as a yellow solid, (0.55 g, 1.67 mmol, 93% yield). M.P.=128.0–130.2° C. $^1$H NMR (DMSO-d$_6$) δ 7.88–6.84 (m, 9H); 3.73 (br s, 2H); 3.32 (s, 2H); 1.55–1.30 (m, 4H); 0.68 (m, 6H). MS Da/e=330 (MH$^+$), 352 (M+Na$^+$). Calcd. for C$_{19}$H$_{23}$NSO$_2$: C, 69.27; H, 7.04 N, 4.25, S, 9.73. Found: C, 69.06; H, 7.16; N, 4.16; S, 9.56.

EXAMPLE 10
Preparation of 3,3-Dimethyl-2,3-dihydro-5-phenyl-1,5-benzothiazepin-4-one.

(a) Bromopivalic acid

The title compound was prepared from hydroxypivalic acid (TCI America, 50.0 g, 423 mmol) using the procedure for Example 1(c). After removing the HBr under high vacuum the product was obtained (66.42 g, 367 mmol, 87%). $^1$H NMR (DMSO-$d_6$) δ 12.3 (br s); 3.57 (s, 2H); 1.19 (s, 6H). MS Da/e=181 (M), 183 (M+2). Calcd for $C_5H_9O_2Br$: C, 33.17; H, 5.01; Br, 44.13. Found: C, 34.07; H, 5.08; Br, 42.45.

(b) 2-(((2-Aminophenyl)thio)methyl)-2-methylpropionic acid.

Bromopivalic acid (Example 10(a)) (59.4 g, 328 mmol) was reacted with 2-aminothiophenol (41 g, 328 mmol, freshly distilled) according to the procedure for Example 1(d). Column chromatography yielded the title compound (52.3 g, 232 mmol, 71%). $^1$H NMR (DMSO-$d_6$) δ 12.44 (br s, 1H); 7.22 (d, 1H); 6.99 (t, 1H); 6.63 (d, 1H); 6.47 (t, 1H); 5.27 (br s, 2H); 2.88 (s, 2H); 1.14 (s, 6H). MS Da/e=226 (MH$^+$), 208 (M−H$_2$O), 180 (M−CO$_2$). Calcd for $C_{11}H_{15}NSO_2$: C, 58.64; H, 6.71; N, 6.22; S, 14.23. Found: C, 58.41; H, 6.78; N, 6.13; S, 14.29.

(c) 3,3-Dimethyl-2,3-dihydro-1,5-benzothiazepin-4(5H)-one

The title compound was prepared by thermal ring closure of the compound of Example 10(b) (33.4 g, 148 mmol) as outlined for Example 1(e). Column chromatography (25% ethyl acetate/petroleum ether) yielded the product (25.39 g, 122 mmol, 83% yield). M.P.=112.6° C. $^1$H NMR (DMSO-$d_6$) δ 9.71 (s, 1H); 7.40 (d, 1H); 7.23 (t, 1H); 7.11 (d, 1H), 6.96 (t, 1H); 2.95 (s, 2H); 1.18 (s, 6H). MS Da/e=208 (MH$^+$). Calcd for $C_{11}H_{13}NSO$: C, 63.74; H, 6.32; N, 6.76; S, 15.47. Found: C, 63.94; H, 6.37; N, 6.56; S, 15.28.

(d) 3,3-Dimethyl-2,3-dihydro-5-phenyl-1,5-benzothiazepin-4-one.

The N-phenylation of the compound of Example 10(c) (22.0 g, 106 mmol) was accomplished following the procedure for Example 1(f) to yield, after column chromatography, the title compound (28.69 g, 101 mmol, 96% yield). M.P.=103.8° C. $^1$H NMR (DMSO-$d_6$) δ 7.68–6.88 (m, 9H); 3.19 (s, 2H); 1.05 (s, 6H). MS Da/e=284 (MH$^+$), 306 (M+Na$^+$). Calcd for $C_{17}H_{17}NSO$: C, 72.05; H, 6.05; N, 4.94; S, 11.31. Found: C, 71.85; H, 6.13, N, 4.85; S, 11.26.

EXAMPLE 11
Preparation of 3,3-Dimethyl-2,3-dihydro-5-phenyl-1,5-benzothiazepin-4-one-1,1-dioxide.

The oxidation of the compound of Example 10(d) (8.69 g, 30.7 mmol) was accomplished following the procedure for Example 2 to give, after column chromatography and oven drying, a white powder, the product as (8.80 g, 27.9 mmol, 91% yield). M.P.=140.8° C. $^1$H NMR (DMSO-$d_6$) δ 7.95–7.04 (m, 9H); 3.81 (s, 2H); 1.10 (s, 6H). MS Da/e=316 (MH$^+$), 338 (M+Na$^+$). Calcd for $C_{17}H_{17}NSO_3 \times (0.5\ H_2O)$: C, 62.94; H, 5.59; N, 4.32; S, 9.88. Found: C, 62.98; H, 5.28; N, 4.26; S, 9.68.

EXAMPLE 12
Preparation of 3,3-Dimethyl-2,3,4,5-tetrahydro-5-phenyl-1,5-benzothiazepine.

The reduction of the compound of Example 11 (8.88 g, 31.05 mmol) was accomplished following the procedure for Example 3 to give the product, after column chromatography (5% ethyl acetate/petroleum ether), as a yellow oil (8.02 g, 29.77 mmol, 96% yield). $^1$H NMR (DMSO-$d_6$) δ 7.44–6.68 (m, 9H); 3.31 (br s, 2H); 2.65 (s, 2H); 0.93 (s, 6H). MS Da/e=270 (MH$^+$). Calcd for $C_{17}H_{19}NS$: C, 75.79; H, 7.11; N, 5.20; S, 11.90. Found: C, 75.82; H. 7.06; N, 5.28; S, 11.86.

EXAMPLE 13
Preparation of 2,3,4,5-Tetrahydro-3,3-dimethyl-5-phenyl-1,5-benzothiazepine-1,1-dioxide.

The oxidation of the compound of Example 12 (5.66 g, 21.01 mmol) was accomplished following the procedure for Example 4 to give, after column chromatography (20% ethyl acetate/petroleum ether), a white powder (5.56 g, 18.45 mmol, 88% yield). M.P.=168.0–168.6° C. $^1$H NMR (DMSO-$d_6$) δ 7.92–6.83 (m, 9H); 3.66 (br s, 2H); 3.33 (s, 2H); 1.03 (s, 6H). MS Da/e=302 (MH$^+$), 324 (M+Na$^+$). Calcd for $C_{17}H_{19}NSO_2$: C, 67.75; H, 6.35; N, 4.65; S, 10.65. Found: C, 67.85; H, 6.44; N, 4.68; S, 10.71.

EXAMPLE 14
Alternative preparation of (±)-3-n-Butyl-3-ethyl-2,3-dihydro-5-phenyl-1,5-benzothiazepin-4-one.

(a) 2-Anilinobenzenethiol.

This was prepared according to a procedure from H. Gilman and J. Dietrich, J. Am. Chem. Soc. 80 (1958) pp. 380–383. To a solution of phenothiazine (10.0 g, 50.2 mmol) in 50 ml THF was added strips of lithium (2.0 g, 288 mmol) over 45 min. The mixture was stirred for 1 h after which time the solution was pipetted off the unreacted lithium and partitioned between ether and water in a separators funnel. The product was extracted with 4 N NaOH. The ether layer yielded unreacted phenothiazine (4.02 g, 20 mmol, 40%). The aqueous base layer was neutralized to pH 4 and extracted with ether 3 times. The ether layer was dried, concentrated and the residue chromatographed (5% ethyl acetate/petroleum ether) giving the title compound (5.49 g, 27.3 mmol, 55% yield). $^1$H NMR (DMSO-$d_6$) δ 7.65–6.74 (m, 9H). MS Da/e=202 (MH$^+$). Calcd for $C_{12}H_{11}NS$: C, 71.61; H, 5.51; N, 6.96; S. 15.93. Found: C, 71.66; H, 5.46, N, 6.92; S, 15.90.

(b) (±)-2-(((2-Anilinophenyl)thio)methyl)-2-ethylhexanoic acid.

This was prepared by reacting the compound of Example 14(a) (3.06 g, 15.2 mmol) with the compound of Example 1(c) (3.50 g, 15.0 mmol) according to the procedure used to prepare in Example 1(d). Column chromatography (50% ethyl acetate/petroleum ether) gave the title compound (3.70 g, 10.4 mmol, 70%). $^1$H NMR (DMSO-$d_6$) δ 12.48 (br s, 1H); 7.46–6.83 (m, 9H); 3.01 (s, 2H); 1.55–1.03 (m, 8H); 0.73 (m, 6H). MS Da/e=358 (MH$^+$). Calcd for $C_{21}H_{27}NSO_2$: C, 70.55; H, 7.61; N, 3.91; S, 8.96. Found: C, 70.61; H, 7.62; N, 3.85; S, 8.88.

(c) (±)-3-n-Butyl-3-ethyl-2,3-dihydro-5-phenyl-1,5-benzothiazepin-4-one.

The ring closure of the compound of Example 14(b) (0.59 g, 1.65 mmol) was carried out using the procedure for Example 1(e) giving the title compound (0.17 g, 0.51 mmol, 31% yield). $^1$H NMR (DMSO-$d_6$) is identical to product of Example 1(f) described above.

EXAMPLE 15
Preparation of (±)-3-n-Butyl-3-ethyl-2,3-dihydro-8-methoxy-5-phenyl-1,5-benzothiazepin-4-one.

(a) 2-Amino-5-methoxythiophenol

A solution of 2-amino-6-methoxybenzothiazole (36 g, 200 mmol; Aldrich Chemical Co.) and 400 ml 30% aqueous potassium hydroxide was refluxed for 16 h. The dark solution was cooled to 0° C. and neutralized to pH 6 with 50% aqueous acetic acid and stirred for 1 h. The resulting slurry was filtered and the product collected on the filter paper and dried (25.29 g, 81% yield). $^1$H NMR (DMSO-d$_6$) δ 6.91–6.44 (m, 3H), 5.90 (br s, 2H). 3.52 (s, 3H). MS Da/e=154 (M–H).

(b) (±)-3-n-Butyl-3-ethyl-2,3-dihydro-8-methoxy-1,5-benzothiazepin-4(5H)-one.

To a solution of the compound of Example 1(c) (25.1 g, 105.8 mmol) in 150 ml dimethylformamide was added the compound of Example 15(a) (13.7 g, 88.2 mmol) and 13 ml triethylamine. The mixture was stirred overnight and then transferred to a separatory funnel with 200 ml water. The pH was adjusted to 4 with 0.1 N HCl and the product was extracted with 6×50 ml diethyl ether. The ether extracts were pooled, dried and the solvent evaporated to give a viscous oil. To this was added 200 ml tetradecane and 825 mg p-toluenesulfonic acid and the mixture refluxed for 1.5 h. The reaction mixture was cooled and loaded onto a silica gel column and the product eluted with 20% ethyl acetate/petroleum ether (15.15 g, 59% yield). M.P.=100.4° C. $^1$H NMR (DMSO-d$_6$) δ 9.51 (s, 1H); 7.96–6.81 (m, 3H); 3.70 (s, 3H); 2.94 (S, 2H); 1.71–1.39 (mn, 4H); 1.19–1.13 (m, 4H); 0.79 (t, 3H); 0.74 (t, 3H). MS Da/e=294 (MH$^+$). Calcd for $C_{16}H_{23}NSO_2$: C, 65.49; H, 7.90; N, 4.77; S, 10.93. Found: C, 65.39; H. 7.94; N, 4.80; S, 10.85.

(c) (±)-3-n-Butyl-3-ethyl-2,3-dihydro-8-methoxy-5-phenyl-1,5-benzothiazepin-4-one.

The compound of Example 15(b) (11.0 g, 37.5 mmol) was reacted with phenyl iodide using the procedure outlined for Example 1(f) to give the product (13.07 g, 94% yield). $^1$H NMR (DMSO-d$_6$) δ 7.54–6.79 (m, 8H); 3.75 (s, 3H); 3.11 (s, 2H); 1.51–1.13 (m, 8H); 0.77 (m, 6H). MS Da/e=370 (MH$^+$). Calcd for $C_{22}H_{27}NSO_2 \times 0.75$ H$_2$O: C, 68.99; H, 7.50; N, 3.66; S, 8.35. Found: C, 68.95; H, 7.14; N, 3.63; S, 8.25.

EXAMPLE 16

Preparation of (±)-3-n-Butyl-3-ethyl-2,3,4,5-tetrahydro-8-methoxy-5-phenyl-1,5-benzothiazepine.

The compound of Example 15(c) (2.25g, 6.10 mmol) was reacted with AlH$_3$ using the procedure outlined for Example 3 to give the product (1.95 g, 90% yield). $^1$H NMR (DMSO-d$_6$) δ 7.11–6.65 (m, 8H,); 3.70 (s, 3H); 3.51 (br s, 2H); 2.66 (s, 2H); 1.40–1.10 (m, 8H); 0.72 (m, 6H). MS Da/e=356 (MH$^+$). Calcd for $C_{22}H_{29}NSO$: C, 74.32; H, 8.22; N, 3.94, S, 9.02. Found: C, 74.20; H. 8.16, N, 3.88; S, 8.95.

EXAMPLE 17

Preparation of (±)-3-n-Butyl-3-ethyl-2,3,4,5-tetrahydro-8-methoxy-5-phenyl-1,5-benzothiazepine-1,1-dioxide.

The compound of Example 16 (1.52 g, 4.28 mmol)was oxidized to the sulfone in analogy with the procedure outlined for Example 4 giving the product (1.61 g, 97% yield). $^1$H NMR (DMSO-d$_6$) δ 7.35–6.79 (m, 8H); 3.80 (s, 3H); 3.65 (br s, 2H); 3.26 (s, 2H); 1.51–1.02 (m, 8H); 0.73 (m, 6H). MS Da/e=388 (MH$^+$). Calcd for $C_{22}H_{29}NSO_3$: C, 68.18; H, 7.54; N, 3.61; S. 8.27. Found: C, 68.13; H, 7.59; N, 3.57; S, 8.21.

EXAMPLE 18

Preparation of (±)-3-n-Butyl-3-ethyl-2,3,4,5-tetrahydro-8-hydroxy-5-phenyl-1,5-benzothiazepine-1,1-dioxide.

To a mixture of aluminum bromide (1M in CH$_2$Cl$_2$, 16 mmol) and ethanethiol (7.4 ml, 100 mmol) at 0° C. was added the compound of Example 17 (0.78 g, 2.01 mmol) in 30 ml CH$_2$Cl$_2$. The mixture was stirred for 1 h at 0° C. and then 25 ml water was added and the product extracted with 3×20 ml CH$_2$Cl$_2$. The organic layer was dried and the solvents evaporated. The residue was applied to a silica gel column and the product eluted with 35% ethyl acetate/petroleum ether (0.74 g, 98%). $^1$H NMR (DMSO-d$_6$) δ 10.00 (s, 1H), 7.28–6.74 (m, 8H); 3.6 (br s, 2H); 3.21 (s, 2H); 1.55–1.02 (m, 8H); 0.73 (m, 6H). MS Da/e=374 (MH$^+$). Calcd for $C_{21}H_{27}NSO_3 \times 0.4$ H$_2$O: C, 66.25; H, 7.36; N, 3.68; S, 8.42. Found: C, 66.12; H. 7.37; N, 3.61; S, 8.30.

EXAMPLE 19

Preparation of (±)-7-Bromo-3-n-butyl-3-ethyl-2,3-dihydro-8-methoxy-5-phenyl-1,5-benzothiazepin-4-one.

(a) (±)-7-Bromo-3-n-butyl-3-ethyl-2,3-dihydro-8-methoxy-1,5-benzothiazepin-4(5H)-one.

To a solution of the compound of Example 15(c) (5.59 g, 19.05 mmol) in methylene chloride (120 ml) at 0° C. was added N-bromosuccinimide (6.78 g, 38.10 mmol) and stirred for 30 min. The reaction mixture was washed once with water and the organic layer was dried, concentrated, and the residue loaded onto a silica gel column. The product was eluted with 10% ethyl acetate/petroleum ether (6.60 g, 93% yield). M.P=102.0° C. $^1$H NMR (DMSO-d$_6$) δ 9.60 (s, 1H); 7.31 (s, 1H); 7.09 (s, 1H), 3.80 (s, 3H); 2.91 (S, 2H); 1.71–1.39 (m, 4H); 1.19–1.13 (m, 4H); 0.80 (t, 3H); 0.75 (t, 3H). MS Da/e=372, 374 (MH$^+$). Calcd for $C_{16}H_{22}BrNSO_2$: C, 51.62; H, 5.96; N, 3.76, S, 8.61. Found: C, 51.33; H. 5.87; N, 3.65; S, 8.44.

(b) (±)-7-Bromo-3-n-butyl-3-ethyl-2,3-dihydro-8-methoxy-5-phenyl-1,5-benzothiazepin-4-one.

To a solution of the compound of Example 19(a) (6.60 g, 17.7 mmol) in bromobenzene (35 ml) was added copper bromide (500 mg) and potassium carbonate (2.5 g), and the mixture was refluxed for 20 h. The reaction mixture was loaded onto a silica gel column and the product eluted with 10% ethyl acetate/petroleum ether (5.05 g, 64% yield). M.P.=131.0–132.8° C. $^1$H NMR (DMSO-d$_6$) δ 7.40–7.05 (m, 7H); 3.88 (s, 3H); 3.14 (s, 2H); 1.55–1.03 (m, 8H); 0.77 (m, 6H). MS Da/e=448, 450 (MH$^+$). Calcd for $C_{22}H_{26}BrNSO_2 \times 0.3H_2O$: C, 58.23; H. 5.91; N, 3.09; Br, 17.61. Found: C, 58.25; H, 5.96; N, 3.05; Br, 17.56.

EXAMPLE 20

Preparation of (±)-7-Bromo-3-n-butyl-3-ethyl-2,3,4,5-tetrahydro-8-methoxy-5-phenyl-1,5-benzothiazepine 1,1-dioxide.

To a solution of AlH$_3$ (29 mmol, generated in situ from H$_2$SO$_4$, 15.5 mmol, and LiAlH$_4$, 29 mmol) in 29 ml diethyl ether was added the compound of Example 19(b) (4.38 g, 9.77 mmol) in 15 ml THF at 0° C. The reaction mixture was allowed to warm to RT over 2 h and was stirred at RT for 15 h after which time TLC (20% ethyl acetate/petroleum ether) showed complete reaction. The reaction flask was cooled to 0° C. and the excess AlH$_3$ was quenched by adding 25 ml of H$_2$O/THF (1:2) dropwise followed by 5 ml 1M NaOH. The mixture was transferred to a separatory funnel and extracted 3 times with ether. The ether extracts were combined, dried, concentrated and column chromatographed (5% ethyl acetate/petroleum ether). The fractions containing product were rotary evaporated and the resulting oil was dissolved in 50 ml tetrahydrofuran and t-butanol. To this solution was added osmium tetroxide (2.5% in 2-methyl-2-propanol, 5.1 ml) and N-methylmorpholine-N-oxide (2.7 g, 22.9 mmol), and the mixture was stirred at RT for 18 h at which point 50 ml NAHCO$_3$ solution was added to neutralize any acid, the mixture transferred to a separatory funnel and extracted 3 times with ethyl acetate. The organic layers were washed with brine, dried (Na$_2$SO$_4$) and concentrated. Column chromatography (10% ethyl acetate/petroleum ether) yielded the product (3.41 g, 7.30 mmol, 75% yield). M.P.=107.5–110.0° C. $^1$H NMR (DMSO-d$_6$) δ 7.42–6.81 (m, 7H); 3.90 (s, 3H); 3.65 (s, 2H); 3.31 (s, 2H); 1.51–0.97 (m, 8H); 0.71 (m, 6H). MS Da/e=466, 468 (MH$^+$). Calcd for C$_{22}$H$_{28}$BrNSO$_3$: C, 56.65; H, 6.05; N, 3.00; S, 6.87. Found: C, 56.80; H, 6.19; N, 3.01; S, 6.80.

EXAMPLE 21

Preparation of (±)-7-Bromo-3-n-butyl-3-ethyl-2,3,4,5-tetrahydro-5-phenyl-1,5-benzothiazepin-8-ol 1,1-dioxide.

The compound of Example 20 (3.19 g, 6.84 mmol) was demethylated using the procedure for Example 18 giving the product (2.48 g, 77% yield). M.P=182.5–183.6° C. $^1$H NMR (DMSO-d$_6$) δ 10.87 (br s, 1H), 7.46–6.82 (m, 7H), 3.62 (br s, 2H); 3.25 (s, 2H); 1.49–1.02 (m, 8H); 0.71 (m, 6H). MS Da/e=452, 454 (MH$^+$). Calcd for C$_{21}$H$_{26}$BrNSO$_3$: C, 55.75; H, 5.79; N, 3.10; S, 7.09. Found: C, 55.79; H, 5.93; N, 3.15; S, 7.17.

EXAMPLE 22

Preparation of (±)-3-n-butyl-3-ethyl-2,3,4,5-tetrahydro-7-methoxy-5-phenyl-1,5-benzothiazepin-8-ol 1,1-dioxide.

To the compound of Example 21 (0.50 g, 1.10 mmol) in ethyl acetate (2.0 ml) and sodium methoxide (10 ml, 25 wt %) was added copper(I) bromide (57 mg) and the mixture was refluxed for 2 h. The reaction mixture was neutralized with 1N HCl and extracted with ether 3×15 ml. The ether extracts were dried and concentrated and the residue was applied to a silica gel column. The product was eluted with 20% ethyl acetate/petroleum ether (0.44 g, 99% yield). $^1$H NMR (DMSO-d$_6$) δ 9.69 (s, 1H), 7.26–6.52 (m, 7H); 3.60 (s, 5H); 1.53–1.02 (m, 8H); 0.71 (m, 6H). MS Da/e=404 (MH$^+$). Calcd for C$_{22}$H$_{29}$NSO$_4$: C, 65.48; H, 7.24; N, 3.47; S, 7.94. Found: C, 65.41; H, 7.26; N, 3.53; S, 8.02.

EXAMPLE 23

Preparation of (±)-3-n-butyl-3-ethyl-2,3,4,5-tetrahydro-7,8-dimethoxy-5-phenyl-1,5-benzothiazepine 1,1-dioxide.

The compound of Example 20 (2.62 g, 5.62 mmol) was treated sodium methoxide using the procedure for Example 22 to give the product (1.95 g, 83% yield). $^1$H NMR (DMSO-d$_6$) δ 7.30 (s, 1H); 7.21–6.79 (m, 5H); 6.52 (s, 1H); 3.80 (s, 3H); 3.62 (br s, 2H); 3.59 (s, 3H); 3.20 (s, 2H); 1.53–0.98 (m, 8H); 0.73 (m, 6H). MS Da/e=418 (MH$^+$). Calcd for C$_{23}$H$_{31}$NSO$_4$: C, 66.16; H, 7.48; N, 3.35; S, 7.68. Found: C, 66.10; H, 7.50; N, 3.42; S, 7.74.

EXAMPLE 24

Preparation of (±)-3-n-butyl-3-ethyl-2,3,4,5-tetrahydro-5-phenyl-1,5-benzothiazepine-7,8-diol 1,1-dioxide.

To sodium hydride (60%, 0.19 g, 4.79 mmol) in dimethylformamide (20 ml) was added ethanethiol (0.35 ml, 4.79 mmol) and the compound of Example 23 (0.50 g, 1.19 mmol). The reaction mixture was refluxed for 3 h, then 25 ml saturated ammnonium acetate (aq) was added, the pH adjusted to 7, and extracted with ethyl acetate 3×10 ml. The organic layer was dried, concentrated and applied to a silica gel column. The product was eluted with 50% ethyl acetate/petroleum ether (0.40 g, 86% yield). $^1$H NMR (DMSO-d$_6$) δ 9.79 (br, 2H); 7.23 (s, 1H); 7.19–6.76 (m, 5H); 6.37 (s, 1H); 3.58 (br s, 2H); 3.11 (s, 2H); 1.50–0.98 (m, 8H); 0.72 (m, 6H). MS Da/e=390 (MH$^+$). Calcd for C$_{21}$H$_{27}$NSO$_4$×0.5 H$_2$O: C, 63.29; H, 7.08; N, 3.51; S, 8.05. Found: C, 63.47; H, 7.21; N, 3.36; S, 7.92.

EXAMPLE 25

Preparation of (±)-7-Bromo-3-n-butyl-3-ethyl-2,3-dihydro-5-phenyl-1,5-benzothiazepin-4-one.

(a) (±)-7-Bromo-3-n-butyl-3-ethyl-2,3-dihydro-1,5-benzothiazepin-4(5H)-one.

To a solution of the compound of Example 1(e) (8.28 g, 31.1 mmol) in acetic acid (30 ml) at RT was added dropwise bromine (1.75 ml, 34.2 mmol) and stirred for 18 h. The reaction mixture was washed once with water, extracted 2×20 ml ether, and the organic layer was dried, concentrated, and the residue loaded onto a silica gel column. The product was eluted with 50% ethyl acetate/petroleum ether (9.23 g, 87% yield). M.P=104.4° C. $^1$H NMR (DMSO-d$_6$) δ 9.81 (s, 1H); 7.58 (s, 1H); 7.42 (d, 1H); 7.04 (d, 1H); 2.96 (S, 2H); 1.73–1.40 (m, 4H); 1.19–1.15 (m, 4H); 0.80 (t, 3H); 0.76 (t, 3H). MS Da/e=342, 344 (MH$^+$). Calcd for C$_{15}$H$_{20}$BrNSO: C, 52.63; H, 5.89; N, 4.09; S, 9.37. Found: C, 52.76; H, 5.93; N, 4.17; S, 9.21.

(b) (±)-7-Bromo-3-n-butyl-3-ethyl-2,3-dihydro-5-phenyl-1,5-benzothiazepin-4-one.

The compound of Example 25(a) (8.8 g, 23.61 mmol) was reacted with phenyl iodide according to the procedure used for Example 1(f) giving product (8.96 g, 91% yield) that is a 3:1 ratio of 7-bromide to 7-iodide that can be coverted entirely to the 7-bromide by treatment with LiBr (10 eq) and copper (I) bromide (10 mol %) in refluxing DMF (18 h). $^1$H NMR (DMSO-d$_6$) δ 7.84 (d, 1H); 7.52 (dd, 1H); 7.37–7.03 (m, 5H); 6.84 (d, 1H); 3.15 (S, 2H); 1.57–1.13 (m, 8H); 0.77 (m, 6H). MS Da/e=418, 420 (MH$^+$). Calcd for C$_{21}$H$_{24}$BrNSO: C, 60.29; H, 5.78, N, 3.35; Br, 19.10. Found: C, 60.56; H, 5.83; N, 3.25; Br, 18.83.

EXAMPLE 26

Preparation of (±)-3-n-butyl-3-ethyl-2,3,4,5-tetrahydro-7-methoxy-5-phenyl-1,5-benzothiazepine 1,1-dioxide.

The compound of Example 25(b) (7.71 g, 18.4 mmol) was reacted with AlH$_3$ using the procedure outlined for Example 3 providing an oil that was directly treated with OsO$_4$ according to the procedure for Example 4. The resulting sulfone was treated with sodium methoxide using the procedure for Example 22 giving the product (67% yield overall for the three steps). $^1$H NMR (DMSO-d$_6$) δ 7.35–6.79 (m, 8H); 3.79 (s, 3H); 3.62 (br s, 2H); 3.26 (s, 2H); 1.53–1.00 (m, 8H); 0.73 (m, 6H). MS Da/e=388 (MH$^+$). Calcd for C$_{22}$H$_{29}$NSO$_3$: C, 68.18; H. 7.54; N, 3.61; S, 8.27. Found: C, 67.89; H, 7.65; N, 3.42; S, 8.20.

EXAMPLE 27

Preparation of (±)-3-n-butyl-3-ethyl-2,3,4,5-tetrahydro-5-phenyl-1,5-benzothiazepin-7-ol 1,1-dioxide.

The compound of Example 26 (1.05 g, 2.71 mmol) was treated with aluminum bromide and ethanethiol according to the procedure for Example 18 giving the title product (0.90 g, 89%). $^1$H NMR (DMSO-d$_6$) δ 9.99 (s, 1H); 7.27–6.74 (m, 8H); 3.61 (br s, 2H); 3.20 (s, 2H); 1.50–1.00 (m, 8H); 0.73 (m, 6H). MS Da/e=374 (MH$^+$). Calcd for C$_{21}$H$_{27}$NSO$_3$× 0.25 H$_2$O: C, 66.73; H, 7.33, N, 3.71, S, 8.48. Found: C, 66.67; H, 7.32; N, 3.67; S, 8.49.

Biological Assay

In vivo inhibition of bile acid reabsorption

Male Spraque-Dawley rats (CD, Charles River) weighing 220–260 gm were housed in individual cages and fed normal chow. The rats were dosed by oral gavage (1 ml/100 gm body weight) with test compounds as a suspension in 0.5% methylcellulose at 9:00 a.m. and 3:30 p.m. for two days. The control group received 0.5% methylcellose. Two hours after the morning dose on day two, the rats were given a trace amount (1.3 nmoles) of 23,25-$^{75}$Se-homocholic acid taurine ($^{75}$SeHCAT) in 1.0 ml saline orally. $^{75}$SeHCAT, a synthetic gamma emitting bile acid analog which is absorbed by the ileal bile acid active uptake system similar to taurocholic acid, has been used clinically as a measure of ileal bile acid absorption. Feces were collected over the 24 hours following $^{75}$SeHCAT administration. Fecal content of $^{75}$SeHCAT was determined using a Packard Auto-Gamma 5000 Series gamma-counter. The % inhibition of bile acid reabsorption is calculated as follows:

$$1 \text{ minus } \frac{\text{total }^{75}SeHCAT\text{-excreted }^{75}SeHCAT \text{ of treated}}{\text{total }^{75}SeHCAT\text{-excreted }^{75}SeHCAT \text{ of control}} \times 100 = \% \text{ inhibition}$$

The percent of inhibition of bile acid reabsorption in the rat using $^{75}$SeHCAT, for the compounds of Examples 2, 4, 7 and 9 at a concentration of 10 mg/Kg was 7, 36, 20 and 29% respectively. In the same test, the compounds of Examples 18, 22, 23, and 27 at a concentration of 1 mg/kg gave between 50 and 65% inhibition of bile acid readsorption.

What is claimed is:

1. The compounds of the formula (I)

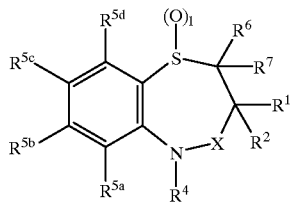

wherein $R^1$ and $R^2$ are the same or different and each is $C_{1-6}$ alkyl group;

$R^4$ is a phenyl group optionally substituted with one to five substituents which are the same or different and are each selected from halogen, hydroxy, nitro, phenyl-$C_{1-6}$ alkoxy, $C_{1-6}$ alkoxy, optionally substituted $C_{1-6}$ alkyl, $S(O)_nR^8$, $CO_2R^8$, $O(CH_2CH_2O)_nR^8$, $OSO_2R^8$, $O(CH_2)_pSO_3R^8$, $(CH_2)_pNR^9R^{10}$ and $O(CH_2)_pN^+R^9R^{11}R^{11}$ wherein $R^8$ to $R^{11}$ are the same or different and are independently selected from hydrogen or optionally substituted $C_{1-6}$ alkyl, and wherein p is an integer from 1–4 and n is an integer from 0–3, and wherein said optionally substituted $C_{1-6}$ alkyl is optionally substituted with hydroxy, halo, $C_{1-6}$ alkyl, $C_{1-6}$ alkoxy, $COR^{12}$, nitrile, $CO_2R^{12}$, $SO_3R^{12}$, $NR^{13}R^{14}$ or $N+R^{13}R^{14} R^{15}$ where $R^{12}$ to $R^{15}$ are the same or different and are selected from H and $C_{1-6}$ alkyl;

$R^{5a}$, $R^{5b}$, $R^{5c}$, and $R^{5d}$ each represent atoms or groups which are the same or different and each is hydrogen, $C_{1-4}$alkoxy, halogen, hydroxy, or $C_{1-4}$alkyl optionally substituted by fluoro;

$R^6$ and $R^7$ are the same or different and each is hydrogen or a $C_{1-6}$alkyl group;

X is $CH_2$, C=O, C=S, or C=$NR^8$ wherein $R^8$ is as hereinbefore defined; and I is an integer from 0–2;

and salts or solvates thereof.

2. A compound of formula (I) according to claim I wherein $R^1$ is methyl or ethyl;

$R^2$ is methyl, ethyl or n-butyl;

$R^4$ is phenyl;

$R^{5a}$ and $R^{5d}$ are hydrogen;

$R^{5b}$ and $R^{5c}$ are the same or different and are each hydrogen, methyl, methoxy, hydroxy, trifluoromethyl or halo;

$R^6$ and $R^7$ are the same or different and are each hydrogen, methyl, ethyl or i-butyl;

X is $CH_2$ or C=O;

I is 2;

or a salt or solvate thereof.

3. A compound of formula (I) which is selected from the group consisting of (±)-3-n-Butyl-3-ethyl-2,3-dihydro-5-phenyl-1,5-benzothiazepin-4-one;

(±)-3-n-Butyl-3-ethyl-2,3-dihydro-5-phenyl-1,5-benzothiazepin-4-one-1,1-dioxide;

(±)-3-n-Butyl-3-ethyl-2,3,4,5-tetrahydro-5-phenyl-1,5-benzothiazepine;

(±)-3-n-Butyl-3-ethyl-2,3,4,5-tetrahydro-5-phenyl-1,5-benzothiazepine-1,1-dioxide;

(±)-3-n-Butyl-2-isobutyl-3-ethyl-2,3,4,5-tetrahydro-5-phenyl-1,5-benzothiazepine-1,1-dioxide;

3,3-Diethyl-2,3-dihydro-5-phenyl-1,5-benzothiazepin-4-one;

3,3-Diethyl-2,3-dihydro-5-phenyl-1,5-benzothiazepin-4-one 1,1-dioxide;

3,3-Diethyl-2,3,4,5-tetrahydro-5-phenyl-1,5-benzothiazepine;

3,3-Diethyl-2,3,4,5-tetrahydro-5-phenyl-1,5-benzothiazepine-1,1-dioxide;

3,3-Dimethyl-2,3-dihydro-5-phenyl-1,5-benzothiazepin-4-one;

3,3-Dimethyl-2,3-dihydro-5-phenyl-1,5-benzothiazepin-4-one-1,1-dioxide;

3,3-Dimethyl-2,3,4,5-tetrahydro-5-phenyl-1,5-benzothiazepine;

3,3-Dimethyl-2,3,4,5-tetrahydro-5-phenyl-1,5-benzothiazepine-1,1-dioxide;

(±)-3-n-Butyl-3-ethyl-2,3,4,5-tetrahydro-7,8-dimethoxy-5-phenyl-1,5-benzothiazepine-1,1-dioxide;

3,3-Diethyl-2,3,4,5-tetrahydro-7,8-dimethoxy-5-phenyl-1,5-benzothiazepine-1,1-dioxide;

(±)-3-n-Butyl-3-ethyl-2,3,4,5-tetrahydro-8-methoxy-5-phenyl-1,5-benzothiazepine-1,1-dioxide;

3,3-Diethyl-2,3,4,5-tetrahydro-8-methoxy-5-phenyl-1,5-benzothiazepine-1,1-dioxide;

(±)-3-n-Butyl-3-ethyl-2,3,4,5-tetrahydro-5-phenyl-1,5-benzothiazepin-8-ol-1,1-dioxide;

3,3-Diethyl-2,3,4,5-tetrahydro-5-phenyl-1,5-benzothiazepin-8-ol-1,1-dioxide;

(±)-3-n-Butyl-3-ethyl-2,3,4,5-tetrahydro-7-methoxy-5-phenyl-1,5-benzothiazepin-8-ol-1,1-dioxide;

3,3-Diethyl-2,3,4,5-tetrahydro-7-methoxy-5-phenyl-1,5-benzothiazepin-8-ol-1,1-dioxide;

(±)-7-bromo-3-n-Butyl-3-ethyl-2,3,4,5-tetrahydro-8-methoxy-5-phenyl-1,5-benzothiazepine-1,1-dioxide;

7-bromo-3,3-Diethyl-2,3,4,5-tetrahydro-8-methoxy-5-phenyl-1,5-benzothiazepine-1,1-dioxide;

(±)-3-n-Butyl-3-ethyl-2,3,4,5-tetrahydro-5-phenyl-1,5-benzothiazepin-7,8-diol-1,1-dioxide;

3,3-Diethyl-2,3,4,5-tetrahydro-5-phenyl-1,5-benzothiazepin-7,8-diol-1,1-dioxide;

(±)-3-n-Butyl-3-ethyl-2,3,4,5-tetrahydro-8-methoxy-5-phenyl-1,5-benzothiazepine-1-monoxide;

3,3-Diethyl-2,3,4,5-tetrahydro-8-methoxy-5-phenyl-1,5-benzothiazepine-1-monoxide;

(±)-3-n-Butyl-3-ethyl-2,3,4,5-tetrahydro-5-phenyl-1,5-benzothiazepin-8-ol-1-monoxide;

3,3-Diethyl-2,3,4,5-tetrahydro-5-phenyl-1,5-benzothiazepin-8-ol-1-monoxide;

(±)-3-n-Butyl-3-ethyl-2,3-dihydro-8-methoxy-5-phenyl-1,5-benzothiazepin-4-one;

(±)-3-n-Butyl-3-ethyl-2,3,4,5-tetrahydro-8-methoxy-5-phenyl-1,5-benzothiazepine;

(±)-3-n-Butyl-3-ethyl-2,3,4,5-tetrahydro-8-methoxy-5-phenyl-1,5-benzothiazepine-1,1-dioxide;

(±)-3-n-Butyl-3-ethyl-2,3,4,5-tetrahydro-8-hydroxy-5-phenyl-1,5-benzothiazepine-1,1-dioxide;

(±)-7-Bromo-3-n-butyl-3-ethyl-2,3-dihydro-8-methoxy-5-phenyl-1,5-benzothiazepin-4-one;

(±)-7-Bromo-3-n-butyl-3-ethyl-2,3,4,5-tetra hydro-8-methoxy-5-phenyl-1,5-benzothiazepine 1,1-dioxide;

(±)-7-Bromo-3-n-butyl-3-ethyl-2,3,4,5-tetrahydro-5-phenyl-1,5-benzothiazepin-8-ol 1,1-dioxide;

(±)-3-n-butyl-3-ethyl-2,3,4,5-tetrahydro-7-methoxy-5-phenyl-1,5-benzothiazepin-8-ol 1,1-dioxide;

(±)-3-n-butyl-3-ethyl-2,3,4,5-tetrahydro-7,8-dimethoxy-5-phenyl-1,5-benzothiazepine 1,1-dioxide;

(±)-3-n-butyl-3-ethyl-2,3,4,5-tetrahydro-5-phenyl-1,5-benzothiazepine-7,8-diol 1,1-dioxide;

(±)-7-Bromo-3-n-butyl-3-ethyl-2,3-dihydro-5-phenyl-1,5-benzothiazepin-4-one;

(±)-3-n-butyl-3-ethyl-2,3,4,5-tetrahydro-7-methoxy-5-phenyl-1,5-benzothiazepine 1,1-dioxide; and (±)-3-n-butyl-3-ethyl-2,3,4,5-tetrahydro-5-phenyl-1,5-benzothiazepin-7-ol 1,1-dioxide.

4. A compound of formula (I) selected from:

(±)-3-n-butyl-3-ethyl-2,3,4,5-tetrahydro-7-methoxy-5-phenyl-1,5-benzothiazepin-8-ol 1,1-dioxide; and (±)-3-n-Butyl-3-ethyl-2,3,4,5-tetrahydro-8-hydroxy-5-phenyl-1,5-benzothiazepine 1,1-dioxide or a salt or solvate thereof.

5. A method of treating a clinical condition in a mammal for which a bile acid uptake inhibitor is indicated which comprises, administering to a mammal an effective bile acid uptake inhibition amount of a compound of formula (I) according to claim I or of a pharmaceutically acceptable salt or solvate thereof.

6. A method of treating a hyperlipidemic condition in a mammal which comprises, administering to the mammal an effective hyperlipidemic treatment amount of compound of formula (I) according to claim 1 or of a pharmaceutically acceptable salt or solvate thereof.

7. The method of claim 6 wherein the hyperlipidemic condition is atherosclerosis.

8. A pharmaceutical composition comprising a compound of formula (I) according to claim 1 or a pharmaceutically acceptable salt or solvate thereof, and at least one pharmaceutically acceptable carrier.

9. A process for the manufacture of a compound of formula (I) according to claim 1, or a salt or solvate thereof, which comprises:

reacting a compound of formula (III)

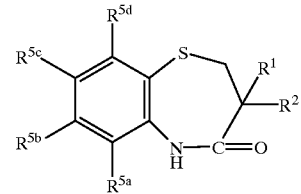

(III)

wherein $R^1, R^2$ and $R^{5a,b,c,d}$ are as hereinbefore defined, with the appropriate $R^4$-Z wherein $R^4$ is as hereinbefore defined and Z is a suitable leaving group.

10. The process according to claim 9, further comprising the steps:

(i) when I is to be 1 or 2, oxidation of the thio moiety; and/or (ii) when X is to be C=S, conversion of the C=O moiety; and/or (iii) when X is to be $CH_2$, reduction of the C=O moiety; and/or (iv) when $R^6$ and/or $R^7$ are to be other than hydrogen, reaction with the appropriate compound of formula $R^6$-Z and/or $R^7$-Z wherein $R^6$, $R^7$, and Z are as hereinbefore defined, and/or (v) optional conversion of the resulting compound of formula(I) to a salt or solvate thereof, and/or (vi) optional resolution of any optical isomers of the compound of formula (I).

11. The compound of formula (I) according to claim 1, wherein $R^1$ is ethyl and $R^2$ is n-butyl.

12. The compound of formula (I) according to claim 1, wherein $R^4$ is phenyl.

13. The compound of formula (I) according to claim 1, wherein $R^{5a}$ and $R^{5d}$ are hydrogen, and $R^{5b}$ and $R^{5c}$ are the same of different and are each selected from the group consisting of hydrogen, methyl, methoxy, hydroxy, trifluoromethyl and halo.

14. The compound of formula (I) according to claim 1, wherein $R^6$ and $R^7$ are both hydrogen.

15. A process for the manufacture of a compound of formula (I) according to claim 1, or a salt or solvate thereof, where X is $CH_2$, said process comprising reducing the carbonyl group of a compound of formula (II)

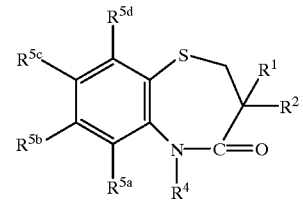

(II)

wherein $R^1$, $R^2$, $R^4$, $R^{5a}$, $R^{5b}$, $R^{5c}$, and $R^{5d}$ are as hereinbefore defined.

* * * * *